(12) United States Patent
Kangawa et al.

(10) Patent No.: US 9,233,143 B2
(45) Date of Patent: Jan. 12, 2016

(54) MEDICINAL AGENT FOR PREVENTING EXACERBATION OF MALIGNANT TUMOR, COMPRISING COMBINATION OF NATRIURETIC PEPTIDE RECEPTOR GC-A AND GC-B AGONISTS

(75) Inventors: Kenji Kangawa, Osaka (JP); Hiroshi Hosoda, Osaka (JP); Takashi Nojiri, Osaka (JP); Meinoshin Okumura, Osaka (JP); Mayumi Furuya, Kobe (JP)

(73) Assignees: National Cerebral and Cardiovascular Center, Suita-shi, Osaka (JP); Osaka University, Suita-shi, Osaka (JP); Shionogi & Co., Ltd., Osaka-shi, Osaka (JP)

( * ) Notice: Subject to any disclaimer, the term of this patent is extended or adjusted under 35 U.S.C. 154(b) by 0 days.

(21) Appl. No.: 14/239,301

(22) PCT Filed: Aug. 17, 2012

(86) PCT No.: PCT/JP2012/070932
§ 371 (c)(1),
(2), (4) Date: May 12, 2014

(87) PCT Pub. No.: WO2013/027680
PCT Pub. Date: Feb. 28, 2013

(65) Prior Publication Data
US 2014/0248269 A1    Sep. 4, 2014

(30) Foreign Application Priority Data
Aug. 19, 2011   (JP) .................................. 2011-179751

(51) Int. Cl.
*A61K 38/22* (2006.01)
*A61K 45/06* (2006.01)
(52) U.S. Cl.
CPC ............. *A61K 38/22* (2013.01); *A61K 38/2242* (2013.01); *A61K 45/06* (2013.01)
(58) Field of Classification Search
None
See application file for complete search history.

(56) References Cited

U.S. PATENT DOCUMENTS

| 2005/0209139 | A1* | 9/2005 | Vesely ............................. 514/12 |
| 2010/0184680 | A1 | 7/2010 | Bevec |
| 2010/0249017 | A1* | 9/2010 | Bevec et al. .................... 514/1.4 |
| 2010/0305031 | A1* | 12/2010 | Wakabayashi et al. ......... 514/6.9 |
| 2010/0310561 | A1* | 12/2010 | Canada et al. ............. 424/134.1 |
| 2011/0039777 | A1 | 2/2011 | Vesely |
| 2011/0300071 | A1* | 12/2011 | Woodard ............. A61K 49/085 424/1.69 |

FOREIGN PATENT DOCUMENTS

| EP | 2682128 A1 | 1/2014 |
| JP | 2010539068 A | 12/2010 |
| WO | WO2006076471 | * 8/2006 |
| WO | WO2009033733 | * 3/2009 ............. A61K 38/08 |

OTHER PUBLICATIONS

Vesely et al., Urodilatin and four cardiac hormones decrease human renal carcinoma cell numbers, Eur. J. Clan. Investig. 36, 810-819, 2006.*
Eichbaum et al., Cardiac and kidney hormones cure up to 86% of human small-cell lung cancers in mice, Eur. J. Clin. Investig., 38, 562-570, 2008.*
Zips et al., New Anticancer Agents: In Vitro and In Vivo Evaluation, In Vivo, 19, 1-8, 2005.*
English Translation—International Preliminary Report on Patentability mailed Feb. 25, 2014 issued in PCT Application No. PCT/JP2012/070932.
EP Application No. 12825866.2, Supplementary European Search Report mailed Feb. 16, 2015.
Vesely, et al., "Five cardiac hormones decrease the number of human small-cell lung cancer cells", *European Jounal of Clinical Investigation*, Jun. 1, 2005, vol. 35, No. 6, pp. 388-398.
Smalley, et al., "Targeting the stromal fibroblasts: a novel approach to melanoma therapy", *Expert Review of Anticancer Therapy*, Dec. 1, 2005, vol. 5, No. 6, pp. 1069-1078.
Orimo, et al., "Stromal Fibroblasts in Cancer: A Novel Tumor-Promoting Cell Type", *Cell Cycle* Aug. 1, 2006, vol. 5, No. 15, pp. 1597-1601.
Krejci, et al., "Interaction of fibroblast growth factor and C-natriuretic peptide signaling in regulation of chondrocyte proliferation and extracellular matrix homeostasis", *Journal of Cell Science*, Nov. 1, 2005, vol. 118, No. 21, pp. 5089-5100.
LeBeau, et al., "Targeting the cancer stroma with a fibroblast activation protein-activated promelitten protoxin", *Molecular Cancer Therapeutics*, May 1, 2009, vol. 8, No. 5, pp. 1378-1386.
Brennen, et al., "Rational Behind Targeting Fibroblast Activation Protein Expressing Carcinoma-Associated Fibroblasts as a Novel Chemotherapeutic Strategy", *Molecular Cancer Therapeutics*, Feb. 1, 2012, vol. 11, No. 2, pp. 257-266.
Garbers, et al., "Membrane guanylyl cyclase receptors: an update", *Trends in Endocrinology and Metabolism*, Aug. 1, 2006, vol. 17, No. 6, pp. 251-258.

(Continued)

*Primary Examiner* — Elly-Gerald Stoica
(74) *Attorney, Agent, or Firm* — Drinker Biddle & Reath LLP

(57) ABSTRACT

Provided are a medicinal agent which is highly safe for use as the treatment of a malignant tumor and is capable of efficiently treating a malignant tumor, that is, a medicinal agent for treating a malignant tumor or for suppressing or preventing the exacerbation thereof, comprising at least one kind of natriuretic peptide receptor GC-A agonist and at least one kind of natriuretic peptide receptor GC-B agonist to be administered in combination; a therapeutic method comprising administering the agent; etc.

5 Claims, 11 Drawing Sheets

(56) References Cited

OTHER PUBLICATIONS

Knights, et al., "De-regulated FGF receptors as therapeutic targets in cancer", *Pharmacology and Therapeutics*, Jan. 1, 2010, vol. 125, No. 1, pp. 105-117.

PCT/JP2012/070932-International Search Report mailed Sep. 25, 2012.

Savoie, et al., "C-type natriuretic peptide and brain natriuretic peptide inhibit adenylyl cyclase activity: interactions with ANF-R2/ANP-C receptors", FEBS Letters, Aug. 14, 1995, vol. 370, No. 1-2, pp. 6-10.

Murakami, et al., "C Type Natrium Rinyo Peptide wa Ko Ensho Sayo, Ko Sen'ika Sayo ni yori Mouse Hai Sen'isho o Keigen Saseru" The Journal of Japanese Respiratory Society, Apr. 10, 2005, vol. 43, p. 150 (POS116)—English translation attached entitled "C-type natriuretic peptide having anti-inflammatory and anti-fibrotic effects ameliorated pulmonary fibrosis in mice".

Nakagawa, et al., "Role of cancer-associated stromal fibroblasts in metastatic colon cancer to the liver and their expression profiled", Oncogene, 2004, Vo. 23, pp. 7366-7377.

Giannoni, et al., "Reciprocal Activation of Prostate Cancer Cells and Cancer-Associated Fibroblasts Stimulated Epithelial-Mesenchymal Transition and Cancer Stemness", Cancer Research. 2010, vol. 70. No. 17, pp. 6945-6956.

Silver, Mark A., "The natriuretic peptide system; Kidney and cardiovascular effects", Curr. Opin. Nephrol. Hypertens., 2006, No. 15, pp. 14-21.

Yoshibayashi, et al., "Brain natriuretic peptide versus atrial natriuretic peptide—physiological and pathophysical significance in children and adutls: a review", Eur. J. Endocrinol., 1996, vol. 135, pp. 265-268.

Horio, et al., "Gene Expression, Secretion, and Autocrine Action of C-Type Natriuretic peptide in Cultured Adult Rat Cardiac Fibroblasts", Endocrinology, 2003, vol. 144, pp. 2279-2284.

Vesely, et al., "Four peptide hormones decrease the number of human breast adenocarcinoma cells", Eur. J. Clin. Invest., 2005, vol. p. 35, pp. 60-69.

* cited by examiner

MEDICINAL AGENT FOR PREVENTING EXACERBATION OF MALIGNANT TUMOR, COMPRISING COMBINATION OF NATRIURETIC PEPTIDE RECEPTOR GC-A AND GC-B AGONISTS

CROSS REFERENCE TO RELATED APPLICATIONS

This application is a National Stage of International Application No. PCT/JP2012/070932, filed Aug. 17, 2012, and which claims benefit of Japanese Patent Application No. 2011-179751 filed Aug. 19, 2011, both of which are incorporated by reference herein.

REFERENCE TO A SEQUENCE LISTING

The instant application contains a Sequence Listing which has been submitted electronically in ASCII format and is hereby incorporated by reference in its entirety. Said ASCII copy, created on Mar. 12, 2015, is named 210630-0002-00-US-509726_SL.txt and is 15,406 bytes in size.

TECHNICAL FIELD

The present invention provides a medicinal agent for efficiently treating a malignant tumor or suppressing or preventing the exacerbation thereof, the agent comprising a combination of a natriuretic peptide receptor GC-A agonist and a natriuretic peptide receptor GC-B agonist; a method for treating a malignant tumor using the same; a method for efficiently treating a malignant tumor, the method comprising using the agent in combination with another antitumor agent etc.; and the like.

BACKGROUND ART

Tumors are classified roughly into two categories, benign tumors and malignant tumors. A malignant tumor is characterized by that the tumor cells have, in addition to growth ability, the abilities of invasion into the surrounding tissue and metastasis to distant organs.

Often mistaken is that malignant tumor tissue consists of cancer cells only, but actually, as shown in FIG. 11, the tumor tissue consists of a mixture of cancer cells and cancer stroma. Cancer-associated fibroblasts (hereinafter sometimes abbreviated to CAFs) are known as typical cells that constitute cancer stroma. Cancer cells and CAFs stimulate each other to, for example, accelerate the growth of the cancer cells and allow the acquisition of metastatic ability and invasive ability by the cancer cells through epithelial mesenchymal transition (hereinafter sometimes abbreviated to EMT), forming a vicious circle in which the exacerbation of a tumor is promoted. That is, for example, humoral factors including cytokines and growth factors produced by cancer stromal cells stimulate cancer cells to promote the production of humoral factors from the cancer cells. Such stimulation by the cytokine etc. is known to further increase the production of humoral factors by the cancer stromal cells, leading to a vicious circle which promotes the exacerbation of the tumor. It has been revealed that CAFs show biological activities and a gene expression pattern different from those of normal fibroblasts (Non Patent Literature 1), and it is also known that CAFs play an important role in the above-mentioned vicious circle (Non Patent Literature 2). However, many of the properties are still unknown, and researches are proceeding today.

Many of antitumor agents are targeted at tumor cells only and show merely a limited effect on cancer stromal cells. Therefore, even when an antitumor agent is administered, humoral factors produced from cancer stromal cells stimulate the exacerbation of tumor cells and often allows the tumor cells to survive, which is a decisive factor for preventing the radical cure of a malignant tumor by use of an antitumor agent.

Natriuretic peptides include atrial natriuretic peptide (ANP), brain natriuretic peptide (BNP), and C-type natriuretic peptide (CNP). These peptides are known to bind specifically to receptors having a guanylate cyclase domain and increase intracellular cGMP to express various physiological activities. The receptors have two types, namely natriuretic peptide receptor GC-A (also known as NPR-A) and natriuretic peptide receptor GC-B (also known as NPR-B), and it is known that ANP and BNP specifically bind to GC-A, and that CNP specifically binds to GC-B (Non Patent Literature 3).

ANP is a 28-amino acid peptide having a cyclic structure and is produced in and secreted from atrial cells. The peptide shows diuretic action in the kidney, and the action of relaxing and dilating vascular smooth muscles in blood vessels. In addition, ANP exerts antagonizing actions against the renin-angiotensin-aldosterone system and vasopressin. These actions comprehensively reduce the load on the heart through lowering the blood pressure, body fluid volume, etc. BNP is a 32-amino acid peptide having a cyclic structure. It was first found in the brain, but later research revealed that the peptide is produced and secreted mainly in ventricular cells rather than the brain. The peptide has similar actions to those of ANP. ANP and BNP specifically bind to GC-A and thereby promote production of cGMP to express the above-mentioned actions (Non Patent Literature 4). Indeed, the secretion of ANP is promoted with elevation of atrial filling pressure in congestive cardiac failure etc., and ANP alleviates the symptoms of congestive cardiac failure etc. via the above-mentioned actions. Human ANP (hANP) is clinically used as a therapeutic agent for acute cardiac failure in Japan. Also, the secretion of BNP is increased in cardiac failure patients, and BNP alleviates various symptoms associated with cardiac failure via the above-mentioned actions. Human BNP (hBNP) is approved as a therapeutic agent for acute cardiac failure in the United States etc.

CNP is a physiologically active peptide found in porcine brain, and it is known that mammals have in their bodies a 22-amino acid peptide CNP-22 and a 53-amino acid peptide CNP-53, which is an N-terminally elongated form of CNP-22. CNP was originally considered to function as a neuropeptide, but the following research revealed that the peptide also exists in peripheral tissues and plays an important role in the process of bone growth. It has been confirmed so far that CNP controls the differentiation and growth of chondrocytes mainly in the growth plate cartilage, and therefore CNP is a promising therapeutic agent for dwarfism including achondroplasia. Further, CNP is known to exert various physiological actions in locations other than the bone and the cartilage. Known actions of CNP on fibroblasts are as follows. CNP is expressed in cardiac fibroblasts and the expression level is increased as a result of stimulation by various inflammatory cytokines. CNP then suppresses DNA synthesis in cardiac fibroblasts and the fibroblasts' production of extracellular matrices, such as collagen, leading to suppression of cardiac fibrosis (Non Patent Literature 5). However, the action of CNP on malignant tumors and cancer stromal cells is unknown.

ANP and BNP are also known to have various physiological activities besides blood-pressure regulating actions including diuretic action, vasodilating action, etc. Regarding tumors, experimental reports have been submitted by Vesely et al. on the growth-suppressing effect of ANP on tumor cells (for example, Non Patent Literature 6 etc.). These reports indicate that, in addition to ANP, long acting natriuretic peptide, vessel dilator, kalliuretic peptide, etc., of which the amino acid sequences are not likely to contribute to binding to the natriuretic peptide receptor GC-A, have the same or stronger growth-suppressing activity on cancer cells as compared to the growth-suppressing activity of ANP whereas BNP does not have such a growth-suppressing activity. From this, it is considered that the growth-suppressing activity of ANP on tumor cells reported by Vesely et al. is not based on the agonist activity for GC-A. The actions of ANP and BNP related to the metastasis of cancer cells are still unknown even after the release of the reports by Vesely et al., and combinational use of ANP and/or BNP with CNP for treating a malignant tumor have not ever been reported.

CITATION LIST

Non Patent Literature

[NPL 1] Nakagawa H, et al., *Oncogene*, 2004, vol. 23, 7366-7377
[NPL 2] Giannoni E., et al., *Cancer Research*, 2010, vol. 70, No. 17, 6945-6956
[NPL 3] Silver M A, *Curr. Opin. Nephrol. Hypertens.*, 2006, vol. 15, 14-21
[NPL 4] Yoshibayashi M. et al., *Eur. J. Endocrinol.*, 1996, vol. 135, 265-268
[NPL 5] Horio T, et al., *Endocrinology*, 2003, vol. 144, 2279-2284
[NPL 6] Vesely B A et al., *Eur. J. Clin. Invest.*, 2005, vol. 35, 60-69

SUMMARY OF INVENTION

Technical Problem

An objective of the present invention is to provide a medicinal agent, a therapeutic method, etc. that are highly safe for use as the treatment of a malignant tumor and are capable of efficiently treating a malignant tumor or suppressing or preventing the exacerbation thereof.

Solution to Problem

The present inventors made extensive research on medicinal agents for more efficiently treating a malignant tumor and found the following:
(i) a natriuretic peptide receptor GC-B agonist acts on cancer-associated fibroblasts (CAFs), which are representative cancer stromal cells, to suppress their production of humoral factors, such as various growth factors and inflammatory cytokines that exacerbate a malignant tumor,
(ii) a natriuretic peptide receptor GC-A agonist suppresses EMT of cancer cells and specifically suppresses cancer cells' production various growth factors, inflammatory cytokines, etc. that exacerbate a malignant tumor,
(iii) simultaneous addition of a natriuretic peptide receptor GC-A agonist and a natriuretic peptide receptor GC-B agonist to co-culture of cancer cells and CAFs significantly suppresses the production of various growth factors, inflammatory cytokines, etc. that exacerbate a malignant tumor, and suppresses EMT of the cancer cells, and
(iv) simultaneous administration of a natriuretic peptide receptor GC-A agonist and a natriuretic peptide receptor GC-B agonist to a mouse to which cancer cells and CAFs have been simultaneously and subcutaneously injected significantly suppresses the growth of tumor tissue.

Based on these findings, the present inventors conducted further research and completed the present invention.

The present invention provides the following.

(1) The present invention provides a medicinal agent for treating a malignant tumor or for suppressing or preventing the exacerbation thereof, comprising at least one kind of natriuretic peptide receptor GC-A agonist and at least one kind of natriuretic peptide receptor GC-B agonist to be administered in combination. The present invention also provides a method for treating a malignant tumor or for suppressing or preventing the exacerbation thereof, comprising administering an effective amount of at least one kind of natriuretic peptide receptor GC-A agonist and an effective amount of at least one kind of natriuretic peptide receptor GC-B agonist in combination (hereinafter, the "method for treating a malignant tumor or for suppressing or preventing the exacerbation thereof" can be referred to as "a therapeutic method etc."); and further provides at least one kind of natriuretic peptide receptor GC-A agonist and at least one kind of natriuretic peptide receptor GC-B agonist to be administered in combination for use in such therapy etc.

Regarding such a medicinal agent etc., the natriuretic peptide receptor GC-A agonist and the natriuretic peptide receptor GC-B agonist may be comprised as an active ingredients in different formulations and administered simultaneously or at different timings. Alternatively, the GC-A agonist and the GC-B agonist may be comprised in a single formulation. The medicinal agent may be in the form of a kit formulation comprising both of the natriuretic peptide receptor GC-A agonist and the natriuretic peptide receptor GC-B agonist. Further, in the medicinal agent etc. of the present invention, the natriuretic peptide receptor GC-A agonist and the natriuretic peptide receptor GC-B agonist may be provided as a single substance having both the activities of the GC-A agonist and the GC-B agonist.

(2) The present invention also provides a medicinal agent for treating a malignant tumor or for suppressing or preventing the exacerbation thereof, the agent comprising at least one kind of natriuretic peptide receptor GC-A agonist as an active ingredient and being to be administered in combination with a natriuretic peptide receptor GC-B agonist; a therapeutic method in such a manner, etc. In this case, the medicinal agent etc. may be administered to, for example, a subject under treatment with a natriuretic peptide receptor GC-B agonist.

(3) The present invention also provides a medicinal agent for treating a malignant tumor or for suppressing or preventing the exacerbation thereof, the agent comprising at least one kind of natriuretic peptide receptor GC-B agonist as an active ingredient and being to be administered in combination with a natriuretic peptide receptor GC-A agonist; a therapeutic method in such a manner, etc. In this case, the medicinal agent etc. may be administered to, for example, a subject under treatment with a natriuretic peptide receptor GC-A agonist.

(4) The present invention also provides a medicinal agent for enhancing the action of a natriuretic peptide receptor GC-B agonist for treating a malignant tumor or suppressing or preventing the exacerbation thereof, the agent comprising at least one kind of natriuretic peptide receptor GC-A agonist as an active ingredient and being to be administered in combination with a natriuretic peptide receptor GC-B agonist; a therapeutic method in such a manner, etc. In this case, the medicinal agent comprising a natriuretic peptide receptor GC-A agonist as an active ingredient is administered to, for example, a subject under treatment with a natriuretic peptide receptor GC-B agonist.

(5) The present invention also provides a medicinal agent for enhancing the action of a natriuretic peptide receptor GC-A agonist for treating a malignant tumor or suppressing or preventing the exacerbation thereof, the medicinal agent comprising at least one kind of natriuretic peptide receptor GC-B agonist as an active ingredient and being to be administered in combination with the natriuretic peptide receptor GC-A agonist; a therapeutic method in such a manner, etc. In this case, the medicinal agent comprising a natriuretic peptide receptor GC-B agonist as an active ingredient is administered to, for example, a subject under treatment with a natriuretic peptide receptor GC-A agonist.

(6) In the medicinal agent etc. provided by the present invention, the natriuretic peptide receptor GC-A agonist is preferably a substance which is any one selected from the following (a1) to (a6) or a pharmacologically acceptable salt thereof and which has an agonist activity for the natriuretic peptide receptor GC-A:
(a1) an atrial natriuretic peptide,
(a2) a brain natriuretic peptide,
(a3) a substance comprising an active fragment of (a1) or (a2),
(a4) a mutant having substitution, deletion, insertion, and/or addition of one to several amino acids in any one of the amino acid sequences of (a1) to (a3),
(a5) a derivative of any one of (a1) to (a4), and
(a6) a modified form of any one of (a1) to (a5).

Here, further preferred examples of the natriuretic peptide receptor GC-A agonist are shown below.

The atrial natriuretic peptide (a1) is preferably a peptide consisting of the amino acid sequence of SEQ ID NO: 1 or 2 in the sequence listing. The brain natriuretic peptide (a2) is preferably a peptide consisting of the amino acid sequence of SEQ ID NO: 3, 4, or 5 in the sequence listing. The active fragment (a3) is preferably a fragment having the amino acid sequence of SEQ ID NO: 6 in the sequence listing, and more preferably a fragment consisting of the amino acid sequence from position 7 to position 27 of SEQ ID NO: 1 or 2 in the sequence listing, the amino acid sequence from position 10 to position 30 of SEQ ID NO: 3 or 4, or the amino acid sequence from position 23 to position 43 of SEQ ID NO: 5 in the sequence listing. The mutant (a4) preferably consists of any one of the amino acid sequences of SEQ ID NOs: 1 to 5 in the sequence listing having substitution, deletion, insertion, and/or addition of one to several amino acids at one to several positions not corresponding to the amino acids shown in SEQ ID NO: 6 in the sequence listing. More preferably, the mutant is (i) a peptide consisting of the amino acid sequence of SEQ ID NO: 1 or 2 having substitution, deletion, insertion, and/or addition of one to several amino acids at any one to several positions selected from positions 1 to 6 and 28, (ii) a peptide consisting of the amino acid sequence of SEQ ID NO: 3 or 4 having substitution, deletion, insertion, and/or addition of one to several amino acids at any one to several positions selected from positions 1 to 9, 31 and 32, or (iii) a peptide consisting of the amino acid sequence of SEQ ID NO: 5 having substitution, deletion, insertion, and/or addition of one to several amino acids at any one to several positions selected from positions 1 to 22, 44 and 45. The derivative (a5) preferably a peptide comprising any one of the amino acid sequences of SEQ ID NOs: 1 to 5 in the sequence listing, more preferably further comprises at least one of partial sequences derived from an Fc region of an immunoglobulin, a serum albumin, or the C terminus of ghrelin, and furthermore preferably comprises any one of the amino acid sequences of SEQ ID NOs: 12, 13, and 14. The modified form (a6) preferably comprises anyone of the amino acid sequences of SEQ ID NOs: 1 to 5 in the sequence listing, in which at least one amino acid not corresponding to the amino acids shown in SEQ ID NO: 6 is chemically modified. More preferably, the modified form is prepared by chemical modification by addition of a pharmaceutically usable polymer.

(7) In the medicinal agent etc. provided by the present invention, the natriuretic peptide receptor GC-B agonist is preferably any one selected from the following (b1) to (b5) or a pharmacologically acceptable salt thereof and which has an agonist activity for the natriuretic peptide receptor GC-B:
(b1) a c-type natriuretic peptide,
(b2) a substance comprising an active fragment of (b1),
(b3) a mutant having substitution, deletion, insertion, and/or addition of one to several amino acids in the amino acid sequence of (b1) or (b2),
(b4) a derivative of any one of (b1) to (b3), and
(b5) a modified form of any one of (b1) to (b4).

Here, further preferred examples of the natriuretic peptide receptor GC-B agonist are shown below.

The C-type natriuretic peptide (b1) is preferably a peptide consisting of the amino acid sequence of SEQ ID NO: 7 (hCNP-22), SEQ ID NO: 8 (hCNP-53), SEQ ID NO: 9 (CNP of fowl origin), or SEQ ID NO: 10 (CNP of frog origin) in the sequence listing. The active fragment (b2) is preferably a peptide having the amino acid sequence of SEQ ID NO: 11 in the sequence listing, and more preferably a peptide consisting of the amino acid sequence from position 6 to position 22 of the amino acid sequence of SEQ ID NO: 7 (hCNP6-22) in the sequence listing. The mutant (b3) consists of any of the amino acid sequences of SEQ ID NOs: 7 to 10 having substitution, deletion, insertion, and/or addition of one to several amino acids at one to several positions not corresponding to the amino acids shown in sequence of SEQ ID NO: 11, and is more preferably (i) a peptide consisting of the amino acid sequence of SEQ ID NO: 7, 9, or 10 having substitution, deletion, insertion, and/or addition of one to several amino acids at any one to several positions selected from positions 1 to 5, or (ii) a peptide consisting of the amino acid sequence of SEQ ID NO: 8 having substitution, deletion, insertion, and/or addition of one to several amino acids at any one to several positions selected from positions 1 to 36. The derivative (b4) preferably is a peptide comprising any one of the amino acid sequences of SEQ ID NOs: 7 to 11 in the sequence listing, and optionally further comprising at least one of partial sequences derived from an Fc region of an immunoglobulin, a serum albumin, or the C terminus of ghrelin. More preferably, the derivative (b4) is a peptide comprising the amino acid sequence of SEQ ID NO: 15, 16, 17, 18, 19, 20, 21, 22, 23, 24, or 25 in the sequence listing. The modified form (b5) preferably comprises any one of the amino acid sequences of SEQ ID NOs: 7 to 10 in the sequence listing, and at least one amino acid not corresponding to the amino acids shown in SEQ ID NO: 11 is chemically modified. More preferably, the modified form is prepared by chemical modification by addition of a pharmaceutically usable polymer.

(8) The present invention also provides a medicinal agent for treating a malignant tumor or for suppressing or preventing the exacerbation thereof, wherein the combination of the natriuretic peptide receptor GC-A agonist and the natriuretic peptide receptor GC-B agonist is administered with another antitumor agent; a therapeutic method in such a manner, etc. In this case, the medicinal agent or the therapeutic method etc. of the present invention wherein the antitumor agent is administered in an amount lower than a normal dosage is also included in the present invention.

Advantageous Effects of Invention

The natriuretic peptide receptor GC-B agonist of the present invention acts on cancer-associated fibroblasts (CAFs) in the tissue of a malignant tumor to suppresses their secretion of humoral factors, such as various growth factors and inflammatory cytokines that exacerbate a malignant tumor, and thus has an effect of suppressing the exacerbation of the tumor. The GC-B agonist in combination with a natriuretic peptide receptor GC-A agonist having an action of suppressing EMT of cancer cells can be applied to the therapy of a malignant tumor and thereby effectively treat the entire tumor tissue by simultaneously suppressing the activities of cancer cells and CAFs as schematically shown in FIG. 12. Such combined use is effective in arresting the progress of the exacerbation of a malignant tumor, for example, the growth, invasion, and metastasis of cancer cells, which are harmful to a living body. Representative GC-A agonists, namely hANP and hBNP, which are biological substances and are already on the market as therapeutic agents with confirmed safety for acute cardiac failure, have the potential to be highly safe medicinal agents. Representative GC-B agonists, namely hCNP-22 and hCNP-53, which are endogenous peptide hormones, can also be applied as highly safe medicinal agents. Further, combining such a agonist with another antitumor agent can enhance the effect of the antitumor agent. Such combined use is effective in controlling a malignant tumor and also can reduce the dosage amount of the antitumor agent, resulting in a decrease in the side effects of the antitumor agent.

Figure 10:
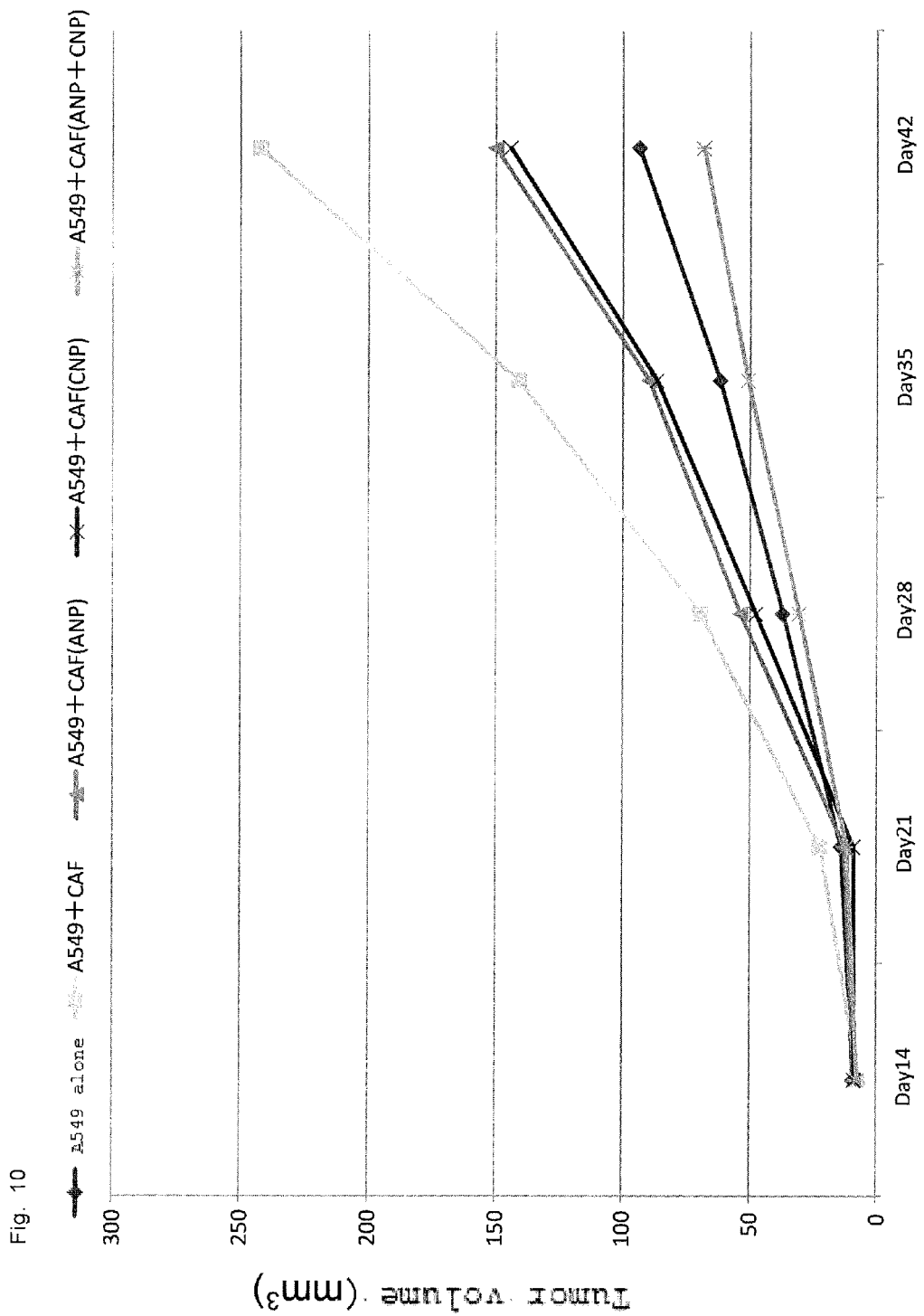

FIG. 10 is a graph showing change in the tumor volume of mice to which a mixed suspension of A549 cells and CAFs was transplanted and for which administration was started 2 weeks after the transplantation (control group (physiological saline: squares), ANP group (hANP was continuously administered at 0.5 µg/kg/min: triangles), CNP group (hCNP-22 was continuously administered at 2.5 µg/kg/min: crosses), ANP+CNP group (hANP and hCNP-22 were continuously administered at 0.5 µg/kg/min and at 2.5 µg/kg/min, respectively: asterisks)). The tumor volume was observed at 14 (starting day of administration), 21, 28, 35 and 42 days after transplantation (diamonds shows the results of a control experiment group, as reference for the administration groups, in which only A549 cells were transplanted to mice (A549 group)). In the graph, the horizontal axis indicates the number of days elapsed after the suspension transplantation and the vertical axis indicates the tumor volume (mm$^3$).

Figure 11:
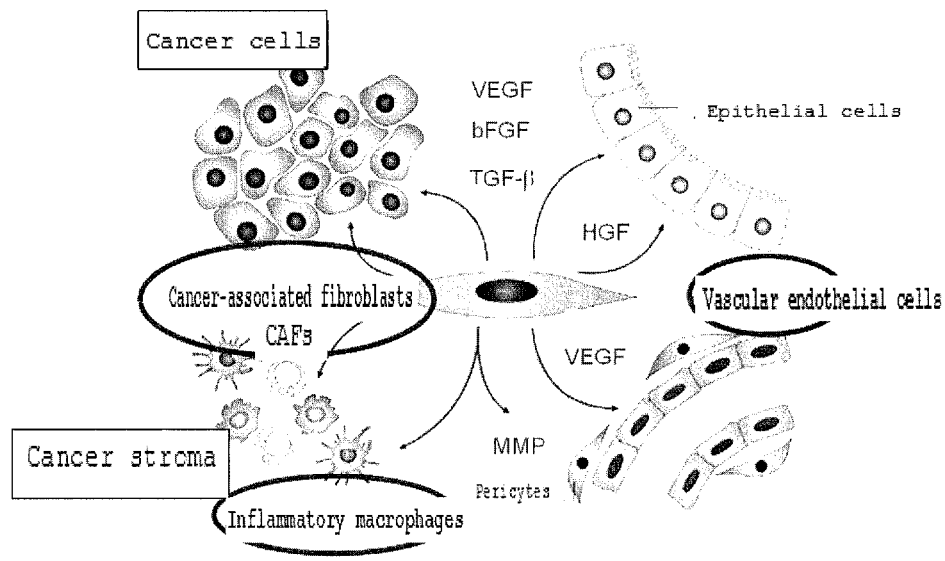

FIG. 11 shows a model of tumor tissue of an actual malignant tumor in a living body.

Figure 12:
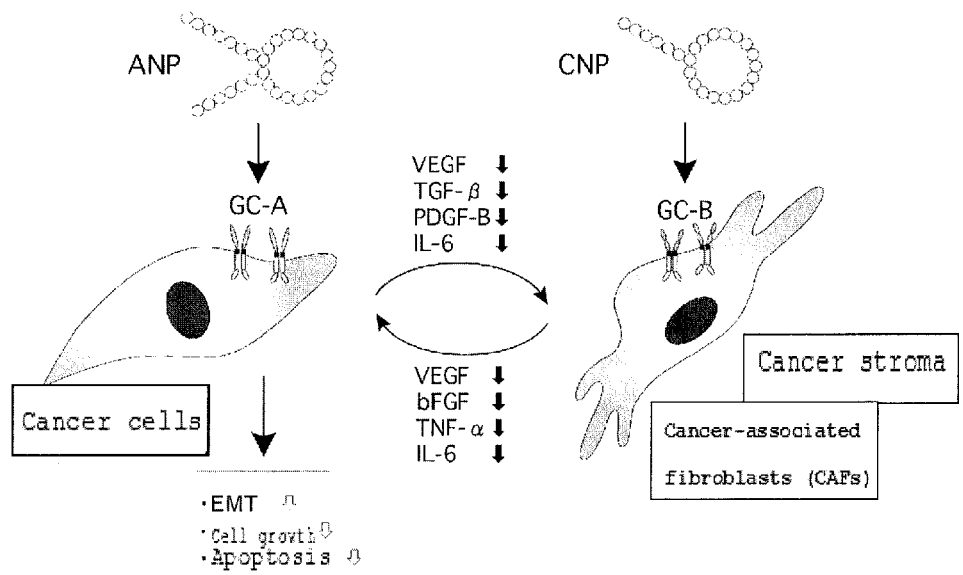

FIG. 12 schematically shows the vicious circle which is formed by cancer cells and cancer-associated fibroblasts (CAFs) and which accelerates the exacerbation of cancer in tumor tissue of an actual malignant tumor in a living body, and the suppressing effect of a GC-A agonist and a GC-B agonist on the vicious circle.

DESCRIPTION OF EMBODIMENTS

In the present invention, the "natriuretic peptide receptor GC-A agonist" means a substance which binds to the natriuretic peptide receptor GC-A (hereinafter, may be simply written as "GC-A" (Chinkers M, et al., *Nature* 338; 78-83, 1989)) and which then exhibits an action to activate the guanylate cyclase of GC-A (hereinafter, "GC-A agonist activity"), and such a substance may be simply written as "GC-A agonist" herein. Representative examples of the GC-A agonist include atrial natriuretic peptide (ANP), brain natriuretic peptide (BNP), etc. The GC-A agonist of the present invention is not particularly limited as long as it has a GC-A agonist activity, and ANP, BNP, an active fragment thereof, a mutant thereof, a derivative thereof, and a modified form thereof may be used. In addition, peptides and low-molecular compounds which have a GC-A agonist activity are included in the GC-A agonist of the present invention even if they do not have any structure in common with ANP or BNP. The medicinal agent of the present invention may comprise one or more kinds of GC-A agonists. The agent preferably comprises 5 kinds or less, more preferably 3 kinds or less, and furthermore preferably one kind of GC-A agonist.

Examples of the ANP in the present invention include a 28-amino acid ANP of human origin (SLRRSSCFGG RMDRIGAQSG LGCNSFRY: SEQ ID NO: 1, herein may be referred to as hANP) and a 28-amino acid ANP of rat origin (SLRRSSCFGG RIDRIGAQSG LGCNSFRY: SEQ ID NO: 2). As an ANP of human origin, the α-hANP described in *Biochem. Biophys. Res. Commun., vol.* 118, p. 131, 1984 has obtained marketing approval in Japan under a generic name of carperitide and is sold under a trade name of HANP. The α-ANP is also generally known as human Pro-ANP [99-126].

Examples of the BNP in the present invention include a 32-amino acid BNP of human origin (SPKMVQGSGC FGRKMDRISS SSGLGCKVLR RH: SEQ ID NO: 3, herein may be referred to as hBNP) a 32-amino acid BNP of porcine origin (SPKTMRDSGC FGRRLDRIGS LSGLGCNVLR RY: SEQ ID NO: 4), and a BNP of rat origin (SQDSAFRIQE RLRNSKMAHS SSCFGQKIDR IGAVSRLGCD GLRLF: SEQ ID NO: 5). The human BNP has obtained pharmaceutical approval in the US etc. under a generic name of nesiritide and is sold under a trade name of Natrecor.

The amino acid sequence Cys-Phe-Gly-Xaa1-Xaa2-Xaa3-Asp-Arg-Ile-Xaa4-Xaa5-Xaa6-Xaa7-Xaa8-Leu-Gly-Cys-Xaa9-Xaa10-Xaa11-Arg (wherein, Xaa3 is Met, Leu, or Ile; and Xaa1, Xaa2, and Xaa4 to Xaa11 are independently naturally occurring amino acids or artificially synthesized amino acid analogs) (SEQ ID NO: 6, hereinafter referred to as "ring structure sequence A") is well conserved among various ANPs and BNPs in the amino acid sequence consisting of a 17-amino acid ring formed by a disulfide bond between two cysteine residues in the sequence (for example, in hANP, the two Cys residues at position 7 and position 23 in SEQ ID NO: 1 bind to each other by disulfide bonding to form a ring structure, and in hBNP, the two Cys residues at position 10 and position 26 in SEQ ID NO: 3 bind to each other by disulfide bonding to form a ring structure) and the amino acid sequence following the C terminus of the ring and thus considered to he important for the binding to a receptor and for the expression of the activity (Silver MA, *Curr. Opin. Nephrol. Hypertens.*, vol. 15, 14-21, 2006; and A. Calderone, *Minerva Endocrinol.*, 29, 113-1.27, 2004).

In the present invention, the "natriuretic peptide receptor GC-B agonist" means a substance which binds to the natriuretic peptide receptor GC-B (hereinafter, may be simply written as "GC-B" (Suga S., et al., *Endocrinology*, 130(1), 229-239, 1992)) to exhibit an action to activate the guanylate cyclase of GC-B (hereinafter, "GC-B agonist activity"), and such a substance may be simply written as "GC-B agonist" herein. Representative examples of the GC-B agonist include c-type natriuretic peptide (CNP). The GC-B agonist of the present invention is not particularly limited as long as it has a GC-B agonist activity, and CNP, an active fragment thereof, a mutant thereof, a derivative thereof, and a modified form thereof may be used. In addition, peptides and low-molecular compounds which have a GC-B agonist activity are included in the agonist of the present invention even if they do not have any structure in common with CNP. The medicinal agent of the present invention may comprise one or more kinds of GC-B agonists. The agent preferably comprises 5 kinds or less, more preferably 3 kinds or less, and further more preferably one kind of GC-B agonist.

Examples of the CNP in the present invention include a 22-amino acid CNP-22 of human origin (GLSKGCFGLK LDRIGSMSGL GC: SEQ ID NO: 7, herein also referred to as hCNP-22, and mammals, such as a porcine, a rat, etc. have this amino acid sequence in common), a 53-amino acid CNP-53 of human origin (DLRVDTKSRA AWARLLQEHP NARKYKGANK KGLSKGCFGL KLDRIGSMSG LGC: SEQ ID NO: 8, herein also referred to as hCNP-53), a CNP of fowl origin (GLSRSCFGVK LDRIGSMSGL GC: SEQ ID NO: 9) and a CNP of frog origin (GYSRGCFGVK LDRIGAFSGL GC: SEQ ID NO: 10).

In various CNPs, the ring structure formed by a disulfide bonding between two cysteine residues in the sequence (for example, in hCNP-22, the two Cys residues at position 6 and position 22 in SEQ ID NO: 7 bind to each other by disulfide bonding to form a ring structure) is considered to be important for the binding to the GC-B receptor and for the expression of the activity (Furuya, M. et al., *Biochem. Biophys. Res. Commun.*, 183 (3),964-969, 1992; Silver MA, *Curr: Opin. Nephrol. Hypertens.*, vol. 15, 14-21, 2006; and A. Calderone, *Minerva Enclocrina.*, 29, 113-127, 2004). Furuya et al. reported that hCNP6-22, which is a peptide consisting of only the ring structure (a peptide consisting of amino acids from position 6 to position 22 of SEQ ID NO: 7), and the ring structure in which the N-terminal and C-terminal sequences of ANP are added to the N-terminus and the C-terminus exhibit a GC-B agonist activity comparable to that of hCNP-22. Furuya et al. also reported that the hCNP-22 having mutations at position 9 (Leu) and position 10 (Lys) has a reduced activity but the peptide having mutations at other positions (for example, at position 17 (Ser) and position 18 Met)) and a peptide obtained by replacing the amino acid sequence from position 10 to position 12 of hANP with the corresponding sequence of hCNP-22, Leu-Lys-Leu (from position 9 to position 11 of SEQ ID NO: 7) exhibit a GC-B agonist activity comparable to that of hCNP-22. Based on the findings, the amino acid sequence of the ring structure important for the GC-B agonist activity is Cys-Phe-Gly-Xaa3-Lys-Leu-Asp-Arg-Ile-Gly-Xaa1-Xaa2-Ser-Gly-Leu-Gly-Cys (wherein, Xaa3 is Leu or Val, Xaa1 is Ser or Ala, and Xaa2 is Met, Phe or Glu: SEQ ID NO: 11), which is hereinafter referred to as "ring structure sequence B".

In the present invention, the "active fragment" of a biologically active peptide or protein means a fragment which consists of the biological activity-related site of the peptide or protein and which retains at least part of the biological activity of the peptide or protein. As an active fragment of the ANP or BNP of the present invention, a peptide which binds to the above-described GC-A and activates the guanylate cyclase of GC-A can be used. Examples of such an active fragment include a peptide comprising the ring structure A (the amino acid sequence of SEQ ID NO: 6), and preferred is a peptide consisting of the ring structure A (the amino acid sequence of SEQ ID NO: 6). Specific examples thereof include a peptide consisting of the amino acid sequence from position 7 to position 27 of SEQ ID NO: 1, the amino acid sequence from position 10 to position 30 of SEQ ID NO: 3 or 4, or the amino acid sequence from position 23 to position 43 of SEQ ID NO: 5, but are not limited thereto. Any fragment which has the ring structure A and has a GC-A agonist activity can be used as the active fragment of the ANP or BNP of the present invention.

As an active fragment of the CNP of the present invention, for example, a peptide which consists of at least part of any of the amino acid sequences of SEQ ID NOs: 7 to 10 and has a GC-B agonist activity can be suitably used. Examples of such an active fragment include a peptide comprising the ring structure B (the amino acid sequence of SEQ ID NO: 11), and preferred is a peptide consisting of the ring structure B (the amino acid sequence of SEQ ID NO: 11). Specific examples thereof include hCNP6-22, a peptide consisting of the amino acid sequence of SEQ ID NO: 7, 9, or 10 in which contiguous amino acids from position 1 to position 5 is partially or completely deleted (i.e., partial or complete deletion of the 1st to the 5th sequence), and a peptide consisting of the amino acid sequence of SEQ ID NO: 8 in which contiguous amino acids from position 1 to position 36 is partially or completely deleted (i.e., partial or complete deletion of the 1st to the 36th sequence), but are not limited thereto. Any fragment which has the ring structure B and has a GC-B agonist activity can be used as the active fragment of the CNP of the present invention.

The GC-A agonist and the GC-B agonist of the present invention may be the above-described active fragment itself, or a peptide in which one or more amino acids are added to the N-terminus, the C-terminus, or both termini of the active fragment (a derivative of the active fragment) as long as the peptide retains the desired agonist activity. Examples of the peptide include a peptide in which a sequence derived from the N-terminal of ANP and/or a sequence derived from the C-terminus of ANP is added to the N-terminus and/or the C-terminus of hCNP6-22 (Furuya, M. et al., *Biochem. Biophys. Res. Commun.*, 183 (3), 964-969, 1992).

In the present invention, the "mutant" of a biologically active peptide or protein means a peptide which has substitution, deletion, insertion and/or addition (hereinafter referred to as "substitution etc.") of one to several amino acids at one to several positions of the amino acid sequence but retains at least part of the biological activity of the original peptide or protein. "Several positions" means usually about 3 positions and preferably about 2 positions. "Several amino acids" means usually about 10 amino acids, preferably about 5 amino acids, more preferably about 3 amino acids, and still more preferably about 2 amino acids. In cases where substitution etc. occurs at two or more positions, the substitution etc. may be any one of substitution, deletion, insertion and addition, or two or more thereof in combination. The amino acid which is subjected to substitution etc. may be a naturally-occurring amino acid, a modified form thereof such as an acylated form, or an artificially synthesized amino acid analog. The position of substitution etc. may be any position as long as part of the activity of the original peptide or protein is retained, but preferred is a position other than a position involved in the active site or the receptor binding site of the original peptide or protein. As a mutant of ANP or BNP, any mutant having substitution etc. at any desired position may be used as long as the GC-A agonist activity is retained. However, preferred examples thereof include a peptide having an amino acid sequence in which the ring structure A mentioned above is retained and substitution etc. occurs outside the ring structure.

For example, a mutant of ANP may have substitution etc. of one to several amino acids at any one to several desired positions in SEQ ID NO: 1 or 2 as long as the GC-A agonist activity is retained. However, a preferred mutant consists of the amino acid sequence of SEQ ID NO: 1 or 2 having substitution etc. of one to several amino acids at one to several positions not corresponding to the amino acids shown in SEQ ID NO: 6, and a more preferred mutant has substitution etc. of one to several amino acids at one to several positions of positions 1 to 6 and 28 in SEQ ID NO: 1 or 2. Also, a mutant of BNP may have substitution etc. of one to several amino acids at any one to several desired positions in SEQ ID NO: 3, 4, or 5 as long as the GC-A agonist activity is retained. However, a preferred mutant consists of the amino acid sequence of SEQ ID NO: 3, 4, or 5 having substitution etc. of one to several amino acids at one to several positions not corresponding to the amino acids shown in SEQ ID NO: 6. More preferred is a peptide having substitution etc. of one to several amino acids at one to several positions of positions 1 to 9, 31, and 32 in SEQ ID NO: 3 or 4, or a peptide having substitution etc. of one to several amino acids at one to several positions of positions 1 to 22, 44, and 45 in SEQ ID NO: 5.

Specific examples of the mutant of ANP include rat α-rANP identical to a hANP having substitution of Ile for Met at position 12 (*Biochem. Biophys. Res. Commun.*, vol. 121, p. 585, 1984), and a hANP having deletion of Ser-Leu-Arg-Arg-Ser-Ser (SEQ ID NO: 26 )at the N-terminus. Examples of such mutants of ANP or BNP include a series of peptides described in *Medicinal Research Review*, vol. 10, p. 115, 1990. Examples of a mutant having deletion of one to several amino acids and substitution of one to several amino acids by other amino acids include mini-ANP consisting of 15 amino acid residues (*Science*, vol, 270, p. 1657, 1995).

As a mutant of CNP, any mutant having substitution etc. at any desired position may be used as long as the GC-B agonist activity is retained. However, preferred examples thereof include a peptide in which the ring structure B mentioned above is retained and substitution etc. occurs outside the ring structure. A specific mutant of CNP may have substitution etc. of one to several amino acids at any one to several desired positions in any of SEQ ID NOs: 7 to 10 as long as the GC-B agonist activity is retained. However, a preferred mutant consists of any of SEQ ID NOs: 7 to 10 having substitution etc. of one to several amino acids at one to several positions not corresponding to the amino acids shown in SEQ ID NO: 11. More preferred is a mutant having substitution etc. of one to several amino acids at one to several positions of positions 1 to 5 in SEQ ID NO: 7, 9, or 10, or a mutant having substitution etc. of one to several amino acids at one to several positions of positions 1 to 36 in SEQ ID NO: 8.

Reported as specific examples of mutants of CNP are as follows: a peptide identical to hCNP-22 having mutations at positions 17 and 18 exhibits a GC-B agonist activity comparable to that of hCNP-22; even a derivative of the mutant having substitution of the N-terminus and the C-terminus of the ring structure by a sequence derived from hANP exhibits about 90% of the GC-B agonist activity of hCNP-22; a peptide identical to hCNP-22 having a mutation at any one position of positions 9 to 11 exhibits 50% or more of the GC-B agonist activity of hCNP-22; a peptide identical to hCNP-22 having mutations at both of positions 10 and 11 exhibits 40% or more of the GC-B agonist activity of hCNP-22; etc. (Furuya, M. et al., *Biochem. Biophys. Res. Commun.*, 183 (3), 964-969, 1992). Another reference describes that various mutants of hCNP-22 retain the GC-B agonist activity and further exhibit resistance to cleavage by neutral endopeptidase (NEP), which is a degrading enzyme of CNP (WO 2009/067639). CD-NP is known as another derivative of hCNP-22. CD-NP is a peptide in which the C-terminal sequence of dendroaspis natriuretic peptide (DNP: a natriuretic peptide derived from snake poison) is added to the C-terminus of hCNP-22 and is known to have both of a GC-A agonist activity and a GC-B agonist activity (Deborah et al., *J. Biol. Chem.*, vol. 289, No. 50, 35003-35009, 2008).

In the present invention, the "derivative" of a biologically active peptide or protein usually means a fusion peptide which comprises the amino acid sequence of the biologically active peptide or protein and to which an added peptide or protein is added and which retains at least part of the biological activity of the physiologically active peptide or protein. A fusion peptide having at least part of such a biological activity (in the present invention, an action of binding to GC-A or GC-B to activate the guanylate cyclase) is also referred to as a derivative of a physiologically active peptide. In the derivative of the present invention, the added peptide may be fused to one or both of the C-terminus and the N-terminus of the original physiologically active peptide or protein. The added peptide is not particularly limited, but preferred is a peptide not having physiological activity in itself. The added peptide may be directly linked or linked via a linker sequence consisting of one to several amino acids. Various linker sequences are known, but preferred are those comprising an abundance of Gly, Ser, etc. Examples of the added peptide include partial sequences derived from an Fc region of an immunoglobulin (preferably IgG), a serum albumin, or the C terminus of ghrelin (for example, a fusion protein in which ANP is linked to an Fc region of an immunoglobulin (see US2010-0310561 A etc.) and a fusion protein in which GLP-1 is linked to serum albumin (see WO2002/046227 etc.)). Examples of the derivative used as the GC-A agonist of the present invention include derivatives of ANP or BNP, derivatives of the active fragments of ANP or BNP, and derivatives of the mutants of ANP or BNP, and preferred are derivatives of hANP and derivatives of hBNP. Examples of the derivative used as the GC-B agonist of the present invention include derivatives of CNP, derivatives of the active fragments of CNP, and derivatives of the mutants of CNP, and preferred are derivatives of hCNP-22, derivatives of hCNP-53, and derivatives of hCNP6-22.

Examples of the derivative used as the GC-A agonist include a fusion protein in which ANP is linked to an Fc region of an immunoglobulin (see US2010-0310561 A etc.). This fusion protein is known to retain the biological activity of ANP and have improved retention in the blood. Examples of the derivatives of ANP and BNP include a series of peptides described in *Medicinal Research Review*, vol. 10, p. 115, 1990.

Specific examples of the derivatives of ANP and CNP include various ANP derivatives and CNP derivatives disclosed in WO2009/142307 (corresponding to US2010-305031 A), In the reference, it is reported that a derivative in which a partial peptide comprising an amino acid sequence represented by General Formula (1): Wk-Xl-Y-Zm-Wn (wherein W is a basic amino acid, such as Lys and Arg; Y is an acidic amino acid, such as Asp and Glu; X and Z may be the same or different and are independently any amino acids other than basic or acidic amino acids; k and n independently represent an integer of 1 or 2; and l and m independently represent a natural number of 0, 1, or 2; preferred examples of the sequence include RKESKK (SEQ ID NO: 27), RKDSKK (SEQ ID NO: 28), RKSEKK (SEQ ID NO: 29), and RKSDKK (SEQ ID NO: 30)) derived from the C-terminus ghrelin was added to a physiologically active peptide, such as ANP, CNP, and motilin, retained the biological activity of the original peptide and had improved retention in the blood. In the present invention, preferred as the partial sequence derived from the C-terminus of ghrelin is an amino acid sequence comprising the above-mentioned sequence represented by General Formula (1) described in WO2009/142307 (corresponding to US2010-305031 A). In WO2009/142307, all of the various derivatives in which the partial peptide derived from the C-terminus of ghrelin was added to one or both of the N-terminus and the C-terminus of hANP retained the GC-A agonist activity and their half-lives in the blood were extended. Such complex ANPs (A), (B), (C) (SEQ ID NOs: 12 to 14), etc. are preferred examples of the ANP derivatives of the present invention. Also, all of the various derivatives in which the partial peptide derived from the C-terminus of ghrelin was added to one or both of the C-terrninus and the N-terminus cif hCNP6-22 retained the GC-B agonist activity and their half-lives in the blood were extended. Such complex CNPs (A) to (K) (SEQ ID NOs: 15 to 25) are preferred examples of the CNP derivatives of the present invention.

For example, in the complex ANP (A) represented by SEQ ID NO: 12 etc., the added partial peptide derived from the C-terminus of ghrelin corresponds to VQQRKESKKPPAKLQPR (SEQ ID NO: 31) (in SEQ ID NO: 12, the amino acid sequence of positions 23 to 45 linked to the C-terminus hANP). In the complex CNP (I) represented by SEQ ID NO: 23, the C-terminal Arg of the added peptide is amidated.

In the complex ANP (C) represented by SEQ ID NO: 14 etc., the added partial peptide derived from the C-terminus of ghrelin corresponds to RPQLKAPPKKSEKRQQV (SEQ ID NO: 32) (in SEQ ID NO: 14, the amino acid sequence of positions 1 to 17 linked to the N-terminus of hANP).

In the complex CNP (E) represented by SEQ ID NO: 19, VQQRKESKKPPAKLQPR (SEQ ID NO: 31) as a partial peptide of ghrelin is added to both of the N-terminus and the C-terminus of CNP. In the complex CNP (F) represented by SEQ ID NO: 20, RPQLKAPPKKSEKRQQV (SEQ ID NO: 32) as a partial peptide of ghrelin is added to the N-terminus of CNP, and VQQRKESKKPPAKLQPR (SEQ ID NO: 31) as a partial peptide of ghrelin is added to the C-terininus thereof.

In the complex CNP (J) represented by SEQ ID NO: 24, the sequence consisting of the amino acids of positions 23 to 39 (VQQRKDSKKPPAKLQPR)(SEQ ID NO:33) is an added partial peptide derived from the C-terminus of ghrelin, and in the complex CNP (K) represented by SEQ ID NO: 25, the amino acid sequence of positions 18 to 36(AGSVDH-KGKQRKVVDHPKR)(SEQ ID NO: 34) is an added partial peptide derived from the C-terminus of ghrelin.

In W02009/142307, besides the complex ANPs and CNPs of SEQ ID NOs: 12 to 25, various complex motilins having similar added partial sequences derived from the C-terminus of ghrelin were examined, and as a result, in the added partial peptide derived from the C-terminus of ghrelin, the sequence represented by General Formula (1) shown above was identified as a core sequence exerting a half-life extending action in the blood. Specific examples of the core sequence include RKESKK(SEQ ID NO: 27) (for example, the amino acid sequence of positions 26 to 31 of SEQ ID NO: 12), the reverse sequence thereof (KKSEKR) (SEQ ID NO: 35), and RKD-SKK (SEQ ID NO: 28) (the amino acid sequence of positions 26 to 31 of SEQ ID NO: 24). Further, based on the findings, a half-life extending partial peptide which comprises the partial peptide as a core sequence (for example, RKSEKK(SEQ ID NO: 29), RKSDKK (SEQ ID NO: 30),etc.) comprised in the amino acid sequence represented by the above general formula is considered to extend the half-lives of physiologically active peptides while maintaining the activities of the peptide. Therefore, such a partial peptide can be used as a partial sequence to be added to the peptide derivatives in the present invention.

Further, a peptide in which the C-terminal part of ANP is added to the C-terminus of hCNP-22 and a peptide in which the N-terminal part and the C-terminal part of ANP are added to the N-terminus and the C-terminus of hCNP6-22 (derivatives of the active fragments of CNP), which are other examples of the derivatives of CNP or the derivatives of the active fragments of CNP, retained the GC-B agonist activity comparable to that of CNP-22 (Furuya, M. et al., *Biochem. Biophys. Res. Commun.*, 183 (3), 964-969, 1992). Further, another reference (WO 2009/067639) describes that various derivatives of hCNP-22 and hCNP-53 retain the GC-B agonist activity, and that some of the derivatives also have resistance to degradation by NEP.

These known derivatives of the natriuretic peptides can be used as the GC-A agonist and/or the GC-B agonist of the present invention.

In the present invention, the "modified form" of a biologically active peptide or protein means a peptide or protein in which amino acids at one to several positions are modified as a result of chemical reaction with another chemical substance and which retains at least part of the biological activity of the peptide or protein. The position to be modified may be any position as long as the activity of the original peptide or protein is retained. In cases where modification is performed by adding a chemical substance which is large to some extent, for example a polymer, the modification preferably occurs at a position which is neither the active site of the peptide or protein nor the receptor binding site of the peptide or protein. In cases where the modification is for prevention of cleavage by a degrading enzyme, a peptide or protein in which the site to be cleaved is modified can be used.

Various methods for chemical modification are known, and example thereof include addition of a polymer which can be used in pharmaceutical technology (pharmacologically usable polymer), such as polyethylene glycol (PEG) and polyvinyl alcohol (PVA), and addition of a compound as a linker to a side-chain amino group of a Lys residue etc. for binding to another protein etc. (for example, serum albumin) via the linker. However, the method for chemical modification is not limited thereto, and various methods can be used. The modified forms of various physiologically active peptides can be produced as needed referring to, for example, US2009-0175821 A etc. Preferred modified forms are prepared by chemical modification by addition of a pharmaceutically usable polymer.

For example, a modified form of ANP may have modification at any one to several desired positions in SEQ ID NO: 1 or 2 as long as the GC-A agonist activity is retained. However, a preferred modified form comprises the amino acid sequence of SEQ ID NO: 1 or 2 and has chemical modification of at least one of its amino acids not corresponding to the amino acids shown in SEQ ID NO: 6. A more preferred modified form consists of the amino acid sequence of SEQ ID NO: 1 or 2 having modification at one to several positions not corresponding to the amino acids shown in SEQ ID NO: 6, and a further more preferred modified form has modification at one to several positions of positions 1 to 6 and 28 in SEQ ID NO: 1 or 2. A mutant of BNP may be modified at any one to several desired positions in SEQ ID NO: 3, 4, or 5 as long as the GC-A agonist activity is retained. However, a preferred modified form comprises the amino acid sequence of SEQ ID NO: 3, 4, or 5 and has chemical modification of at least one of its amino acids not corresponding to the amino acids shown in SEQ ID NO: 6. A more preferred modified form consists of the amino acid sequence of SEQ ID NO: 3, 4, or 5 having modification at one to several positions not corresponding to the amino acids shown in SEQ ID NO: 6, and a further more preferred modified form has modification at one to several positions of positions 1 to 9, 31, and 32 in SEQ ID NO: 3 or 4; or of positions 1 to 22, 44 and 45 in SEQ ID NO: 5. Further, the modified forms of the above-mentioned active fragments and mutants of ANP or BNP, and the modified forms of the derivatives thereof are all included in the present invention. Such various modified forms may be used in the present invention as long as the modified forms retain the GC-A agonist activity.

Specific examples of the modified forms which may be used as a GC-A agonist include various modified forms, for example, one in which a hydrophilic polymer, such as PEG and PVA or a hydrophobic group represented by a hydrocarbon group, such as an alkyl group and an aryl group, is bound to hBNP, or a mutant or an active fragment thereof, and it is known that such modified forms retain the GC-A agonist activity (see U.S. Pat. No. 7,662,773 etc.).

In the binding of ANP or BNP to the GC-A receptor, important parts are the ring structure and the C-terminal tail part of ANP and BNP. Therefore, even another sequence or substance is linked to the N-terminus of ANP or BNP, the added peptide or modifying substance hardly exerts influence on the ring structure, that is, does not inhibit the binding. For this reason, the GC-A agonist activity is retained in such a derivative or a modified form. This fact is proved by the above-mentioned various references.

A modified form of CNP may have modification at any one to several desired positions in any of SEQ ID NOs: 7 to 10 as long as the GC-B agonist activity is retained. The modified form preferably comprises any of the amino acid sequences of SEQ ID NOs: 7 to 10 and has chemical modification of at least one of its amino acids not corresponding to the amino acids shown in SEQ ID NO: 11, and more preferably consists of any of SEQ ID NOs: 7 to 10 having modification at one to several positions not corresponding to the amino acids shown in SEQ ID NO: 11. Further more preferred is a modified form having modification at one to several positions of positions 1 to 5 in SEQ ID NO: 7, 9, or 10. Since it is known that the cleavage by NEP occurs between Cys at position 1 and Phe at position 2 of SEQ ID NO: 11 in the ring structure B of various CNP peptides, in a modification for providing resistance to cleavage by neutral endopeptidase (NEP) for example, the bond between the above residues may be modified.

Further, the modified forms of the above-mentioned active fragments and mutants of CNP, and the modified forms of the derivatives thereof are all included in the present invention. Such various modified forms may be used in the present invention as long as the modified forms retain the GC-B agonist activity.

Regarding specific examples of such modified forms of CNP, an active fragment thereof, a mutant thereof, or a derivative thereof, for example, WO 2009/067639 describes modified forms in which various hydrophilic polymers, such as PEG, are bound to hCNP-22 or hCNP-53, and modified forms in which the peptide bond between Cys6 and Phe7 of hCNP-22 corresponding to the cleavage site by NEP is replaced by a pseudopeptide bond, such as (—CH$_2$—NH—) and (—C(═O)—N(R)—, wherein R represents a lower alkyl group including methyl, ethyl, propyl, isopropyl, n-butyl, isobutyl, sec-butyl, and tert-butyl) and discloses that a plurality of the modified forms retain the GC-B agonist activity and that many of them have longer retention in the blood than hCNP-22. The modified forms of various physiologically active peptides can be produced as needed referring to, for example, US2009-0175821 A etc.

In the binding of CNP to the GC-B receptor, important part is the ring structure of CNP. Therefore, even another sequence or substance is linked to the C-terminus and/or N-terminus of CNP, the added peptide or modifying substance hardly exerts influence on the ring structure, that is, does not inhibit the binding. For this reason, the GC-B agonist activity is retained in such a derivative or a modified form. This fact is proved by the above-mentioned various references.

The above-described ANP, BNP and CNP, an active fragment thereof, a mutant thereof, a derivative thereof, and a modified form thereof may be harvested from natural cells or tissue, produced by a genetic engineering procedure or a cellular engineering procedure, or chemically synthesized. Further, modification of the amino acid residues or partial deletion of the amino acid sequence may be performed by enzymatic or chemical treatment. Such production can be appropriately performed by a conventional method, according to the references mentioned herein.

A person skilled in the art can readily perform measurement using a conventionally known method to determine whether a substance has a GC-A agonist activity. Specific procedure is, for example, as follows. To cultured cells in which GC-A (Chinkers M, et al., Nature, 338; 78-83, 1989) is forcibly expressed, the substance is added, and then the intracellular cGMP concentration is determined. "Retain part of the GC-A agonist activity" usually means that, when a GC-A agonist substance and ANP or BNP (in cases where the agonist substance is one prepared based on the sequence of ANP or BNP, the reference peptide) are measured in a parallel manner for the GC-A agonist activity in the same measurement system, the peak value of the cGMP concentration increasing activity of the agonist substance is at least about 10% or more of that of ANP or BNP. Preferably about 30% or more is retained, more preferably about 50% or more is retained, and further more preferably about 70% or more is retained. A substance having long duration of the activities in a living body can be used for the present invention even if the increase at the peak is not very significant.

A person skilled in the art can readily perform measurement using a conventionally known method to determine whether a substance has a GC-B agonist activity. Specific procedure is, for example, as follows. To cultured cells in which GC-B (Chinkers M, et al., Nature, 338; 78-83, 1989) is forcibly expressed, the substance is added, and then the intracellular cGMP concentration is determined. "Retain part of the GC-B agonist activity" usually means that, when a GC-B agonist substance and CNP are measured in a parallel manner for the GC-B agonist activity in the same measurement system, the peak value of the cGMP concentration increasing activity of the agonist substance is at least about 10% or more of that of CNP. Preferably about 30% or more is retained, more preferably about 50% or more is retained, and furthermore preferably about 70% or more is retained. A substance having long duration of the activities in a living body can be used for the present invention even if the increase at the peak is not very significant.

In addition, a low molecular compound which can improve the cGMP productivity in such an evaluation system when added thereto can be used as a GC-A agonist or a GC-B agonist in the present invention even if the compound (for example, a low-molecular compound) does not have any structure in common with a natriuretic peptide.

Preferred as the GC-A agonist of the present invention is ANP, BNP, an active fragment thereof having the ring structure A, or a mutant thereof having substitution etc. outside the ring structure A, a derivative thereof, or a modified form thereof. More preferred is hANP, hBNP, a derivative thereof, or a modified form thereof, and further more preferred is hANP or hBNP.

Preferred as the GC-B agonist of the present invention is CNP, an active fragment thereof having the ring structure B, or a mutant thereof having substitution etc. outside the ring structure B, a derivative thereof, or a modified form thereof. More preferred is hCNP-22, hCNP-53, an active fragment thereof, namely hCNP6-22, a derivative thereof, or a modified form thereof, and further more preferred is hCNP-22, hCNP-53, or hCNP6-22.

The substance used as an active ingredient in the medicinal agent of the present invention may be a pharmaceutically acceptable salt of the above-described GC-A agonist or GC-B agonist, and preferably a pharmaceutically acceptable salt of hANP, hBNP, or hCNP-22, hCNP-53, or hCNP6-22. That is, in the present invention, the acid addition salts of the above nentioned substances may be used as an active ingredient. Examples of the acid include inorganic acids, such as hydrochloric acid, sulfuric acid, and phosphoric acid, and organic acids, such as formic acid, acetic acid, butanoic acid, succinic acid, and citric acid. Alternatively, in the present invention, the forms of metal salts, such as sodium salt, potassium salt, lithium salt, and calcium salt, and organic base salts of the above mentioned substances may be used as an active ingredient. The active ingredient in the medicinal agent of the present invention may be its related substance in a free state or a pharmaceutically acceptable salt thereof.

As the active ingredient in the medicinal agent of the present invention, a single substance having both the properties of a GC-A agonist and a GC-B agonist (herein, also referred to as "double-active substance") may be used. In the cases where such a double-activity substance is comprised as an active ingredient, the effect of the present invention can be achieved with the substance alone, but depending on the degree of the activity thereof, the GC-A agonist or the GC-B agonist described above may additionally be administered in combination. The double-activity substance is not particularly limited as long as it retains both of the GC-A agonist activity and the GC-B agonist activity. Examples of the substance include a substance having the ring structure A (SEQ ID NO: 6) and the ring structure B (SEQ ID NO: 11) in a single molecule (for example, a fusion peptide comprising both sequences, a modified form in which a peptide consisting of one of the sequences is linked to a peptide consisting of the other sequence via a linker compound), a substance comprising an amino acid sequence having combined properties of the ring structure A and of the ring structure B, etc. As a specific example of the double-activity substance, CD-NP is known. CD-NP is a peptide in which the C-terminal sequence of dendroaspis natriuretic peptide (DNP: a natriuretic peptide derived from snake poison) is added to the C-terminus of hCNP-22 and is known to have both of the GC-A agonist activity and the GC-B agonist activity (Deborah et al., *J. Biol. Chem.*, vol. 289, No. 50, 35003-35009, 2008). Another example is a peptide in which the amino acids at positions 9 to 11 of hANP (SEQ ID NO: 1) are replaced by Leu-Lys-Lue, and this peptide retained both of the GC-A agonist activity and the GC-B agonist activity (Furuya, M. et al., *Biochem. Biophys. Res. Commun.*, 183 (3), 964-969, 1992).

As shown in FIG. 11, the tumor tissue of an actual malignant tumor in a living body does not consist of cancer cells only but exists as a mass in which cancer stroma and cancer cells are mixed. Cancer stroma comprises cancer-associated fibroblasts (CAFs), inflammatory macrophages, vascular endothelial cells, etc. and mostly consists of CAFs.

A GC-A agonist has an effect of suppressing EMT that may trigger the exacerbation of cancer cells. However, the GC-A agonist does not exert its action on cancer stroma represented by cancer-associated fibroblasts (CAFs) existing as a mixture with cancer cells in the tumor tissue of a malignant tumor as shown in FIG. 12. Therefore, when a GC-A agonist is administered alone to a patient with a malignant tumor, the growth factors, cytokines, etc. produced by CAFs stimulate cancer cells, and the EMT-suppressing effect of the GC-A agonist may be attenuated.

Meanwhile, a GC-B agonist has an action of suppressing the increase in the production of growth factors, such as VEGF and PDGF, and cytokines, such as TNF-α and IL-6 responding to stimulation of CAFs by TGF-β etc. However, the GC-B agonist does not exert its action on cancer cells itself, and the effect is unlikely to be sufficiently achieved in the therapy of the tumor tissue of an actual malignant tumor.

The present invention, in which such a GC-A agonist and a GC-B agonist are administered in combination to suppress the activities of cancer cells and CAFs at a time and act on the entire tumor tissue as schematically shown in FIG. 12, is effective in treating a malignant tumor or in suppressing or preventing the exacerbation thereof. The present invention provides a method for treating a malignant tumor or for suppressing or preventing the exacerbation thereof, a medicinal agent therefor, etc., characterized by that such a natriuretic peptide receptor GC-A agonist and a natriuretic peptide receptor GC-B agonist are administered in combination.

A "medicinal agent for combined administration" of multiple active ingredients or drugs means that the active ingredients or drugs are intended to be administered in combination when the medicinal agent is used. In this case, the active ingredients may be comprised in a single formulation or in a product as a kit. Alternatively, the active ingredients may be in separate formulations as different products. In this case, the package insert of the product comprising one active ingredient may describe that the product may be administered in combination with the other active ingredient. The phrase "for combined administration" may be restated as, for example, "in combination", "for combined use", "for combined dosage", "for administration in the same period", "for use in the same therapy", etc.

In the present invention, "combined administration" of multiple active ingredients or drugs means that a subject to receive the administration takes all the combined active ingredients or drugs into the body in a certain period of time. The active ingredients may be administered as a single formulation comprising all the ingredients. Alternatively, the active ingredients may be separately formulated into separate formulations and then separately administered. In cases where the active ingredients are separately formulated, the timing of the administration is not particularly limited. The formulations may be administered simultaneously, at certain time intervals, or on different days. In the present invention, "combined administration" of multiple active ingredients or drugs includes that a double-activity substance acting as both a GC-A agonist and a GC-B agonist is administered alone. In cases where two or more active ingredients are administered at different timings or on different days, the order of the administration of each active ingredient is not particularly limited. Normally, each formulation is administered according to each administration method, and therefore the frequency of the administration may be the same or different among the formulations. In cases where each active ingredient is separately formulated, the administration method (route of administration) may be the same or different among the formulations. It is not necessary that all the active ingredients are present in the body at the same time. As long as all the active ingredients are taken into the body during a certain period of time (for example, one month, preferably one week, more preferably several days, still more preferably one day), it is allowable that one active ingredient has already disappeared from the body when another active ingredient is administered.

Examples of the administration form of the medicinal agent of the present invention, e.g. a medicinal agent for combined administration of at least one kind of natriuretic peptide receptor GC-A agonist and at least one kind of natriuretic peptide receptor GC-B agonist include
1) administration of a single formulation comprising at least one kind of natriuretic peptide receptor GC-A agonist and at least one kind of natriuretic peptide receptor GC-B agonist,
2) simultaneous administration of two kinds of formulations obtained by separately formulating at least one kind of natriuretic peptide receptor GC-A agonist and at least one kind of natriuretic peptide receptor GC-B agonist, via the same administration route,
3) administration of two kinds of formulations obtained by separately formulating at least one kind of natriuretic peptide receptor GC-A agonist and at least one kind of natriuretic peptide receptor GC-B agonist, via the same administration route at a certain time interval,
4) simultaneous administration of two kinds of formulations obtained by separately formulating at least one kind of natriuretic peptide receptor GC-A agonist and at least one kind of natriuretic peptide receptor GC-B agonist, via different administration routes, and
5) administration of two kinds of formulations obtained by separately formulating at least one kind of natriuretic peptide receptor GC-A agonist and at least one kind of natriuretic peptide receptor GC-B agonist, via different administration routes at a certain time interval, (for example, a formulation comprising a natriuretic peptide receptor GC-A agonist as an active ingredient is administered first, and after a certain period of time has elapsed, a formulation comprising at least one kind of natriuretic peptide receptor GC-B agonist as an active ingredient is administered; or the formulations are administered in the reverse order).

In the present invention an "active ingredient" is one of the ingredients comprised in the medicinal agent, and such an active ingredient has at least a part of the desired pharmacological effect of the medicinal agent. The amount/content of the active ingredient in the medicinal agent is not particularly limited, and may be blended at various ratios depending on the strength of the pharmacological effect of the composition.

The medicinal agent of the present invention may comprise ingredients in addition to the active ingredients as long as the effect of the present invention is exerted. Preferably, the medicinal agent is a composition comprising, besides the active ingredients, a publicly known pharmacologically acceptable carrier, excipient, diluent, etc.

The substance used as an active ingredient in the medicinal agent of the present invention or a pharmacologically acceptable salt thereof is preferably mixed with a publicly known pharmacologically acceptable carrier, excipient, diluent, etc., and administered to an individual by an administration method conventionally used in the pharmaceutical field, i.e., oral administration or parenteral administration, such as permucosal administration, intravenous administration, intramuscular administration, and subcutaneous administration.

In cases where the active ingredient is a peptide substance, it may be orally administered as a formulation resistant to degradation in the digestive tract, for example, a microcapsule formulation of liposomes encapsulating the peptide as the active ingredient. The administration can be performed not through the mucosa of the digestive tract but through, for example, the rectal, intranasal, or sublingual mucosa. In this case, the active ingredient can be administered in the form of a suppository, a nasal spray, an inhalant, a sublingual tablet, etc. In the present invention, such formulations may be used that the peptide retention in the blood is improved by adopting various controlled-release formulations or long-acting formulations which comprise a biodegradable polymer represented by polysaccharide such as dextran, polyamine, PEG, etc. as a carrier.

The dosage amount of the substance used as an active ingredient of the medicinal agent of the present invention varies with the type of disease; the age, body weight, and degree of the symptoms of the individual (patient); and the route of administration, but generally the upper limit of the daily dosage of each active ingredient is, for example, about 100 mg/kg or less, preferably about 50 mg/kg or less, and more preferably 1 mg/kg or less. The lower limit of the daily dosage of each active ingredient is, for example, about 0.1 μg/kg or more, preferably 0.5 μg/kg or more, and more preferably 1 μg/kg or more.

The administration frequency of the drug (medicinal agent) of the present invention varies with the active ingredient to be used, the route of administration, and the specific disease to be treated. For example, in cases where a natriuretic peptide is orally administered, 4 times or less daily is preferred. In cases of parenteral administration, for example intravenous administration, continuous administration with the use of an infusion pump, a catheter, etc. is preferred.

In cases where the peptide, such as ANP, BNP, and CNP, or a salt thereof is administered, for example, a lyophilized formulation thereof may be dissolved in water for injection, and then continuously administered with the use of a microinfusion pump (if not available, microinfusion set for children) etc. The duration of the continuous administration is usually several hours to several days, for example, about 1 to 14 days, and preferably about 3 to 7 days. In this case, the upper limit of the dosage of each active ingredient may be appropriately selected in a concentration range of, for example, about 50 μg/kg/min (about 72 mg/kg/day) or less. The dosage may be about 5 μg/kg/min (about 7.2 mg/kg/day) or less, preferably about 0.5 μg/kg/min (about 720 μg/kg/day) or less, more preferably about 0.2 μg/kg/min or less, further more preferably about 0.1 μg/kg/min or less, and further more preferably about 0.05 μg/kg/min or less. The lower limit is usually about 0.0001 μg/kg/min (about 0.144 μg/kg/day) or more, preferably about 0.001 μg/kg/min (about 1.44 μg/kg/day) or more, and more preferably about 0.01 μg/kg/min (about 14.4 μg/kg/day) or more. Specific administration may be, for example, at about 0.025 μg/kg/min for about 3 or 4 days, and in this case, the daily dosage in terms of the active ingredient is about 36 μg/kg.

Since a natriuretic peptide has an effect of relaxing and dilating blood vessels and decreasing the blood pressure as described above, in treating a malignant tumor or in suppressing or preventing the exacerbation thereof, the administration is preferably performed at a rate not decreasing the blood pressure beyond necessity, and monitoring the blood pressure during and immediately after the administration is preferred. In this case, the duration of the administration of hANP etc. is usually a few hours or more, and preferably 1 day or more. For this duration, the administration is preferably continued, and the duration is usually 1 day or more, preferably about 1 to 14 days, and more preferably about 1 to 5 days. In cases where malignant tumors should be controlled for a long period of time, the above-mentioned administration method may be appropriately repeated and the dosage, duration, etc. may be appropriately changed depending on the patient's conditions.

Specifically, in cases where ANP is administered, for example, intravenously, it is preferred that, for example, 1000 μg of hANP (for example, HAMP for INJECTION 1000 (trade name) manufactured by DAIICHI SANKYO Co., Ltd.) is dissolved in 10 mL of water for injection and then administered at a rate of "body weight×about 0.06 mL/hour" (about 0.1 μg/kg/min) or less. The administration rate is not limited to the above rate. Preferably, the administration rate is appropriately adjusted in the range of about 0.2 μg/kg/min or less (preferably about 0.01 μg/kg/min or more) depending on the disease condition, with monitoring of the blood pressure and the heart rate. In particular, about 3- or 4-day continuous administration of hANP at about 0.025 μg/kg/min has been confirmed not to widely change hemodynamic status, such as the blood pressure and the heart rate, and thus this dosage and administration method is also preferably employed.

I in cases where hBNP is administered, for example, intravenously, it is preferred that, for example, hBNP is continuously administered at about 0.01 μg/kg/min, and before the continuous administration, bolus administration of about 2 μg/kg of hBNP may be performed in combination. In this case also, the administration is preferably performed at a rate not decreasing the blood pressure beyond necessity, and monitoring the blood pressure during and immediately after the administration is recommended. In cases where the administration of ANP or BNP at the above rate does not have a significant impact on the blood pressure, heart rate, etc., the administration rate may be further increased.

In the present invention, in addition to hANP, hBNP, etc. currently applied in clinical practice, a natriuretic peptide receptor GC-B agonist, such as CNP, may be administered. In this case, the dosage of CNP may be determined based on the dosages of ANP and BNP, and may be changed as appropriate depending on the disease condition. For example, in the case where hCNP-22 is continuously administered, it is preferred that hCNP-22 is administered, for example, intravenously at a rate of 0.01 to 1.0 µg/kg/min while the rate is appropriately adjusted with monitoring of the blood pressure and the heart rate.

In cases where an active fragment, a mutant, a derivative, or a modified form of ANP, BNP, and/or CNP is used instead of the naturally occurring type (hANP, hBNP, hCNP-22, etc.), the dosage, administration method, administration rate, administration frequency, etc. may be appropriately determined depending on the properties of the substance, such as strength of the activity, retention in the body, and the molecular weight. Regarding the active ingredient, such as hANP or hBNP, and CNP (hCNP-22), the use of controlled-release formulation technique, long-acting formulation technique, or various mutants, derivatives, modified forms, etc. resistant to peptide degradation allows employment of an administration method, administration frequency, etc. which inflicts less suffering on the patient, without limitation to bolus or continuous administration.

The subjects to receive the administration of the medicinal agent of the present invention are usually patients with malignant tumors. The malignant tumor patients may be patients without any other underlying diseases, or patients at high risk of heart failure, for example. The type of the malignant tumor is not particularly limited, and the medicinal agent may be applied to any type of malignant tumor. Preferred as the malignant tumor is one where a natriuretic peptide receptor GC-A is expressed in cancer cells of the malignant tissue, and examples thereof include lung cancer, pancreatic cancer, thyroid cancer, breast cancer, uterine cancer, ovarian cancer, prostatic cancer, colon cancer, esophageal cancer, kidney cancer, bone tumor, brain tumor, etc. Patients with malignant tumors etc. under therapy with at least one of the different antitumor agents described later (antitumor agents other than natriuretic peptide receptor GC-A agonists and natriuretic peptide receptor GC-B agonists) are also preferred subjects to receive the administration in the present invention. The tumor of the patient may be a primary tumor or a metastatic tumor. In the case of a primary tumor, the administration is preferably performed in combination with a tumor tissue removal surgery. Similarly, in the case of a metastatic tumor, if removal surgery is possible, the administration is preferably performed during surgery and following several days in combination with the surgery. If a resection surgery is difficult or metastasis to another organ is suspected, it is preferred to suppress the exacerbation of cancer cells and to control the growth or metastasis by regular or continuous administration. In this case, combined administration of a conventional antitumor agent with the medicinal agent of the present invention enables more efficient control of the malignant tumor. After being used in combination with an antitumor agent for a certain period of time, only a GC-A agonist and a GC-B agonist can be regularly or continuously used. To select a subject to receive the administration of the medicinal agent of the present invention, harvest of tumor tissue may be performed before the administration to check whether a GC-A receptor is expressed in cancer cells and/or whether a GC-B receptor is expressed in cancer-associated fibroblasts. In cases where the expression of the receptors is confirmed, the agent may be administered to the subject.

In addition, when used in combination with at least one kind of another conventionally used antitumor agent, the medicinal agent of the present invention can efficiently treat cancer. Thus the present invention also provides a combined therapy with such an antitumor agent. Since the medicinal agent of the present invention can control the activation and exacerbation of cancer cells and cancer-associated fibroblasts, appropriate administration of the medicinal agent in combination with a therapy using another antitumor agent can increase the efficiency of the therapy and improve the prognosis of the therapy. Further, even when the antitumor agent is administered in an amount lower than a normal dosage, an excellent therapeutic effect can be obtained. The use of the antitumor agent at a low dosage can decrease the amount of total dosage. In this connection, there is an advantage that not only the dosage but also the application frequency or the occurrence of a side effect can be reduced.

Examples of the antitumor agent used in combination include an alkylating agent, an antimetabolite, an antitumor antibiotic, an antitumor plant constituent, a BRM (biological response control substance), a hormone, a vitamin, an anticancer antibody, a molecular target agent, and other antitumor agents.

More specifically, examples of the alkylating agent include alkylating agents, such as nitrogen mustard, nitrogen mustard N-oxide and chlorambucil; aziridine alkylating agents, such as carboquone and thiotepa; epoxide alkylating agents, such as dibromomannitol and dibromodulcitol; nitrosourea alkylating agents, such as carmustine, lomustine, semustine, nimstine hydrochloride, streptozocin, chlorozotocin, and ranimustine; busulfan, improsulfan tosilate, dacarbazine, etc.

Examples of various antimetabolites include purine antimetabolites, such as 6-mercaptopurine, 6-thioguanine, and thioinosin; pyrimidine antimetabolites, such as fluorouracil, tegafur, tegafur-uracil, carmofur, doxifluridine, broxuridine, cytarabine, and enocitabine; folate antimetabolites, such as methotrexate and trimetrexate; etc.

Examples of the antitumor antibiotic include anthracycline antibiotic antitumor agents, such as mitomycin-C, bleomycin, peplomycin, daunorubicin, aclarubicin, doxorubicin, pirarubicin, THP-adriamycin, 4'-epidoxorubicin, and epirubicin; chromomycin A3, actinomycin-D; etc.

Examples of the antitumor plant constituent include vinca alkaloids, such as vindesine, vincristine, and vinblastine; taxanes, such as paclitaxel and docetaxel; epipodophyllotoxins, such as etoposide and teniposide; etc.

Examples of the BRM include a tumor necrosis factor, indomethacin, etc.

Examples of the hormone include hydrocortisone, dexamethasone, methylprednisolone, prednisolone, prasterone, betamethasone, triamcinolone, oxymetholone, nandrolone, methenolone, fosfestrol, ethinylestradiol, chlormadinone, medroxyprogesterone, etc.

Examples of the vitamin include vitamin C and vitamin A.

Examples of the anticancer antibody and the molecular target agent include trastuzumab, rituximab, cetuximab, nimotuzumab, denosumab, bevacizumab, infliximab, imatinib mesilate, gefitinib, erlotinib, sunitinib, lapatinib, sorafenib, etc.

Examples of the other antitumor agents include cisplatin, carboplatin, oxaliplatin, tamoxifen, camptothecin, ifosfamide, cyclophosphamide, melphalan, L-asparaginase, aceglatone, sizofiran, picibanil, procarbazine, pipobroman, neocarzinostatin, hydroxyurea, ubenimex, krestin, etc.

In addition, it has been recently reported that PDE5 inhibitors represented by Viagra (registered trademark) has a suppressing effect on a malignant tumor (Das et al. *Proc. Natl. Acad. Sci.* (2010), vol/107, No. 42, 18202-18207), and the medicinal agent of the present invention can also be used in combination with these PDE5 inhibitors. The PDE5 inhibitor is not particularly limited as long as the substance has an activity to inhibit the degradation of cGMP by a PDE5 enzyme, and various agents can be used (for example, see M. P. Govannoni, et al., *Curr. Med. Chem.*, 17, 2564-2587, 2010). Preferred examples thereof include sildenafil, vardenafil, tadalafil, udenafil, mirodenafil, SLx-2101, lodenafil, lodenafil carbonate, exisulind, and derivatives thereof and pharmacologically acceptable salts thereof. More preferred are sildenafil, vardenafil, tadalafil, udenafil, mirodenafil, and pharmacologically acceptable salts thereof; further more preferred are sildenafil citrate, vardenafil hydrochloride, tadalafil, udenafil, and mirodenafil; and most preferred is sildenafil citrate. These medicinal agents can be produced and formulated according to the above-mentioned references (including references cited therein) and by publicly known techniques.

In the present invention, when an additional antitumor agent is administered in combination with the combination of a natriuretic peptide receptor GC-A agonist and a natriuretic peptide receptor GC-B agonist, the combination of the GC-A agonist and the GC-B agonist and the additional antitumor agent may, as described above, be comprised in a single formulation or separately comprised in different formulations as an active ingredient thereof. The order or the like of administration of the GC-A agonist, the GC-B agonist, and the additional antitumor agent is not particularly limited.

Further, the GC-B agonist in the present invention can enhance the therapeutic effect of such an additional antitumor agent when used in combination with the antitumor agent. That is, the antitumor agent acts on cancer cells and tumor tissue, and the GC-B agonist acts on cancer-associated fibroblasts, and as a result the combination can control the activation and exacerbation of the entire tumor tissue. In this case, a GC-A agonist is not necessarily administered in combination therewith.

The present invention encompasses a medicinal agent for treating a malignant tumor or for suppressing or preventing the exacerbation thereof, the agent comprising at least one kind of natriuretic peptide receptor GC-B agonist as an active ingredient and being to be administered in combination with an additional antitumor agent; a therapeutic or preventive method performed in such a manner, etc.

The present invention encompasses a medicinal agent for enhancing the action of an antitumor agent for treating a malignant tumor or suppressing or preventing the exacerbation thereof, the agent comprising at least one kind of natriuretic peptide receptor GC-B agonist as an active ingredient and being to be used for combined administration with an additional antitumor agent; a therapeutic or preventive method performed in such a manner, etc.

Regarding the above medicinal agents etc., the additional antitumor agent that is not a natriuretic peptide receptor GC-A agonist or a natriuretic peptide receptor GC-B agonist is preferably administered in an amount lower than a normal dosage. The additional antitumor agent is not particularly limited, and the one described above or the like may be used. The GC-B agonist and the antitumor agent may be separately administered as different formulations, comprised in a single formulation, or in the form of a kit.

The present invention also provides a kit for treating a malignant tumor or for suppressing or preventing the exacerbation thereof, the kit comprising a combination of a GC-A agonist and a GC-B agonist. Examples of the kit include a kit comprising a vial in which both of a GC-A agonist, such as hANP or hBNP, or a salt thereof and a GC-B agonist, such as hCNP-22 or hCNP-53, or a salt thereof are encapsulated as lyophilized formulation(s) (which may be encapsulated in a single vial or separate vials), and water for injection to be used for dissolving the formulation(s). In addition, a syringe to be used for dissolving and administering the formulation may be combined, and also a microinfusion pump, a microinfusion set for children, or the like may be combined.

In cases where the GC-A agonist or the GC-B agonist of the present invention is a peptide substance, gene therapy where the GC-A agonist peptide and/or the GC-B agonist peptide is expressed in the patient's body as a result of introduction of a gene which encodes the peptide(s) may be performed. In this case, both agonists may be expressed in the gene therapy. Alternatively, it is allowable that only one of them is expressed by the gene therapy and the other is administered as a formulation from outside the body.

For example, as the ANP gene, a gene comprising a nucleotide sequence which encodes the amino acid sequence of SEQ ID NO: 1 or 2 (for example, the one described in *Science*, vol. 226, 1206, 1984) may be used. As the BNP gene, a gene comprising a nucleotide sequence which encodes the amino acid sequence of SEQ ID NO: 3, 4, or 5 (for example, the one described in *Biochem. Biophys. Res. Commun.*, vol. 165, 650, 1989) may be used. As the CNP gene, a gene comprising a nucleotide sequence which encodes the amino acid sequence of any one of SEQ ID NOs: 7 to 10 (for example, the one described in *Biochem. Biophys. Res. Commun.*, vol. 165, 650, 1989) may be used. When the above-mentioned genes are used for therapy, the genes may be introduced via intramuscular injection or local injection, using a retrovirus, an adenovirus, an adeno-associated virus, or an artificial vector as a vector. Alternatively, without the use of such a vector, the genes may be introduced in the form of a plasmid. Specific gene therapy may be performed by the method described in *Jikken Igaku* (Experimental Medicine) vol. 12, 303, 1994 or a method described in the references cited therein, etc.

The present invention encompasses a medicinal agent for enhancing the action of a natriuretic peptide receptor GC-B agonist for treating a malignant tumor or suppressing or preventing the exacerbation thereof, the agent comprising at least one kind of natriuretic peptide receptor GC-A agonist as an active ingredient and being to be administered in combination with the natriuretic peptide receptor GC-B agonist; and a method for enhancing the action of a natriuretic peptide receptor GC-B agonist for treating a malignant tumor or suppressing or preventing the exacerbation thereof, the method comprising administering the medicinal agent in combination with the natriuretic peptide receptor GC-B agonist. The subjects to receive the administration of the medicinal agent is, for example, a subject under treatment with a natriuretic peptide receptor GC-B agonist. The subject under treatment with a natriuretic peptide receptor GC-B agonist is usually the patients with a malignant tumor as described above.

The present invention encompasses a medicinal agent for enhancing the action of a natriuretic peptide receptor GC-A agonist for treating a malignant tumor or suppressing or preventing the exacerbation thereof, the agent comprising at least one kind of natriuretic peptide receptor GC-B agonist as an active ingredient and being to be administered in combination with the natriuretic peptide receptor GC-A agonist; and a method for enhancing the action of a natriuretic peptide receptor GC-A agonist for treating a malignant tumor or suppressing or preventing the exacerbation thereof, the method comprising administering the medicinal agent in combination with the a natriuretic peptide receptor GC-A agonist. The subjects to receive the administration of the medicinal agent is, for example, a subject under treatment with a natriuretic peptide receptor GC-A agonist. The subject under treatment with a natriuretic peptide receptor GC-A agonist is usually the patients with a malignant tumor as described above.

The natriuretic peptide receptor GC-A agonist and the natriuretic peptide receptor GC-B agonist as active ingredients, the administration method thereof, etc. are the same as those of the medicinal agent described above.

EXAMPLES

Hereinafter, the invention will be specifically described by referring to the Examples below. The Examples are merely illustrative examples of the embodiments of the present invention, and the present invention is not limited thereto.

The experimental materials used in the Examples below were obtained and prepared as follows.

hANP (SEQ ID NO: 1) and hCNP-22 (SEQ ID NO: 7) were produced according to a publicly known method, and hBNP (SEQ ID NO: 3) was obtained from Peptide Institute, Inc. (Osaka). Each of the lyophilized products was dissolved in physiological saline containing IBMX (3-isobutyl-1-methylxanthine). After the concentration was adjusted as needed so that the final concentration of IBMX would be $5 \times 10^{-4}$ M, each solution was used in the following experiments.

Lung adenocarcinoma cell line, A549 cells, was obtained from ATCC (Manassas, Va.). The cells were cultured in DMEM culture medium (Invitrogen, Carlsbad, Va.) containing 10% FCS under 5% $CO_2$ at 37° C. The amounts of the culture medium were 1.5 mL for each well of a 6-well dish, 400 µL for each well of a 24-well dish, and 150 µL for each well of a 96-well dish. In the Examples below, unless otherwise stated, the same culture medium and culture conditions were adopted.

For obtaining CAFs (cancer-associated fibroblasts), tissue harvested from a patient having lung cancer surgery was subjected to primary culture after the consent of the patient was obtained. The cells were then cultured in DMEM culture medium containing 10% FCS under 5% $CO_2$ at 37° C., and the cells of the 5th and earlier passages were used.

TGF-β1 (transforming growth factor β1) was purchased from R&D systems Inc. (Minneapolis, Minn.) and diluted with physiological saline as needed and used for the following experiments.

Example 1

Changes in the Intracellular cGMP Level in Response to Stimulus of Natriuretic Peptide The A549 cells were cultured in a 24-well dish at $4 \times 10^4$ cells/well, and the culture medium was replaced with DMEM culture medium free from FCS the next day. The CAFs were cultured in a 24-well dish at $1 \times 10^4$ cells/well, and the culture medium was replaced with DMEM culture medium containing 1% FCS the next day.

To these culture media, solutions of hANP, hBNP, and hCNP-22 (final concentration: ten-fold serial dilution from $1 \times 10^{-11}$ M to $1 \times 10^{-6}$ M, the same amount of physiological saline was used as a control) were separately added. After 10 minutes had passed, 400 µL of cooled 70% ethanol (containing 0.1 N hydrochloric acid) was added, and ultrasonication was performed for a short time. The treated solution was lyophilized, and the cGMP level was measured using Cyclic GMP Assay kit (made by Yamasa Corp.). The cGMP level measurement results are shown in FIGS. 1A and 1B.

Figure 1:
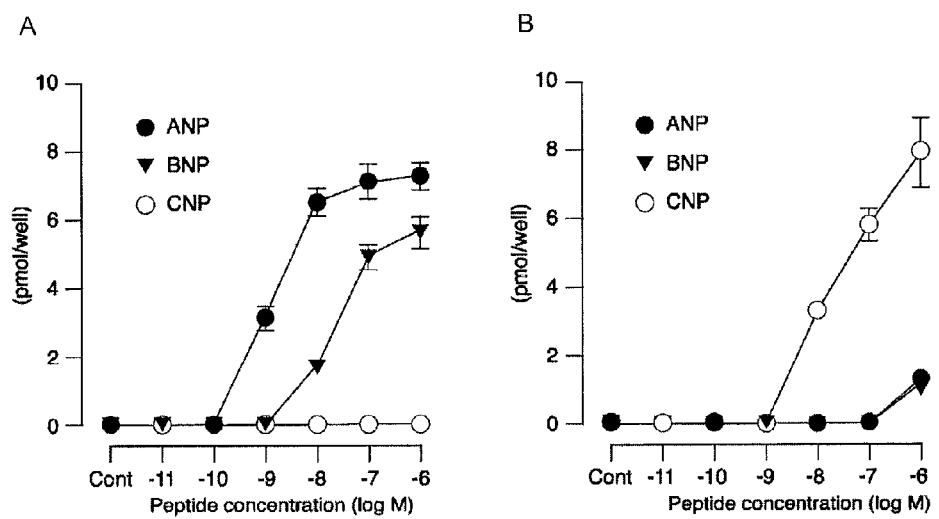
FIG. 1A is a graph showing changes in the intracellular cGMP level responding to stimulation of lung cancer A549 cells by natriuretic peptides (hANP (black circle), hBNP (down-pointing black triangle), and hCNP-22 (white circle)).
FIG. 1B is a graph showing changes in the intracellular cGMP level responding to stimulation of cancer-associated fibroblasts (CAFs) by natriuretic peptides (hANP (blackcircle), hBNP (down-pointing black triangle), and hCNP-22 (white circle)). The number of samples at each point of the graph in FIG. 1A is n=5 to 7, and that in FIG. 1B is n=3 or 4.

As shown in FIG. 1A, hANP and hBNP, which are GC-A agonists, increased the intracellular cGMP level of the A549 cells in a concentration-dependent manner whereas hCNP-22, which is a CG-B receptor agonist that does not bind to the GC-A receptor, did not show such increase. In contrast, as shown in FIG. 1B, hCNP-22 increased the cGMP level of the CAFs in a concentration-dependent manner whereas hANP and hBNP did not show such an action.

Thus, it was revealed that the signalings in A549 cells and CAFs occur in response specific to stimulus from the GC-A receptor and the GC-B receptor, respectively.

Example 2

The Effect of ANP on EMT Induced by TGF-β1

Using a 6-well dish, the A549 cells were cultured at $1 \times 10^5$ cells/well, and the culture medium was replaced with DMEM culture medium free from FBS the next day. After 24 hours of culture, the cells were used in the following experiment.

An ANP group (a hANP solution was added (final concentration: 1 µM)) and a control group (the same amount of physiological saline was added) were prepared, and after 2 hours from the addition (of the hANP solution or the physiological saline) to the A549 cells, TGF-β1 was added so that the final concentration would be 0.125, 0.25, 0.5, 1.0, and 2.0 ng/mL. After 24 hours had passed, the morphological change in the cells was observed under a microscope and photographed (FIG. 2).

Figure 3:
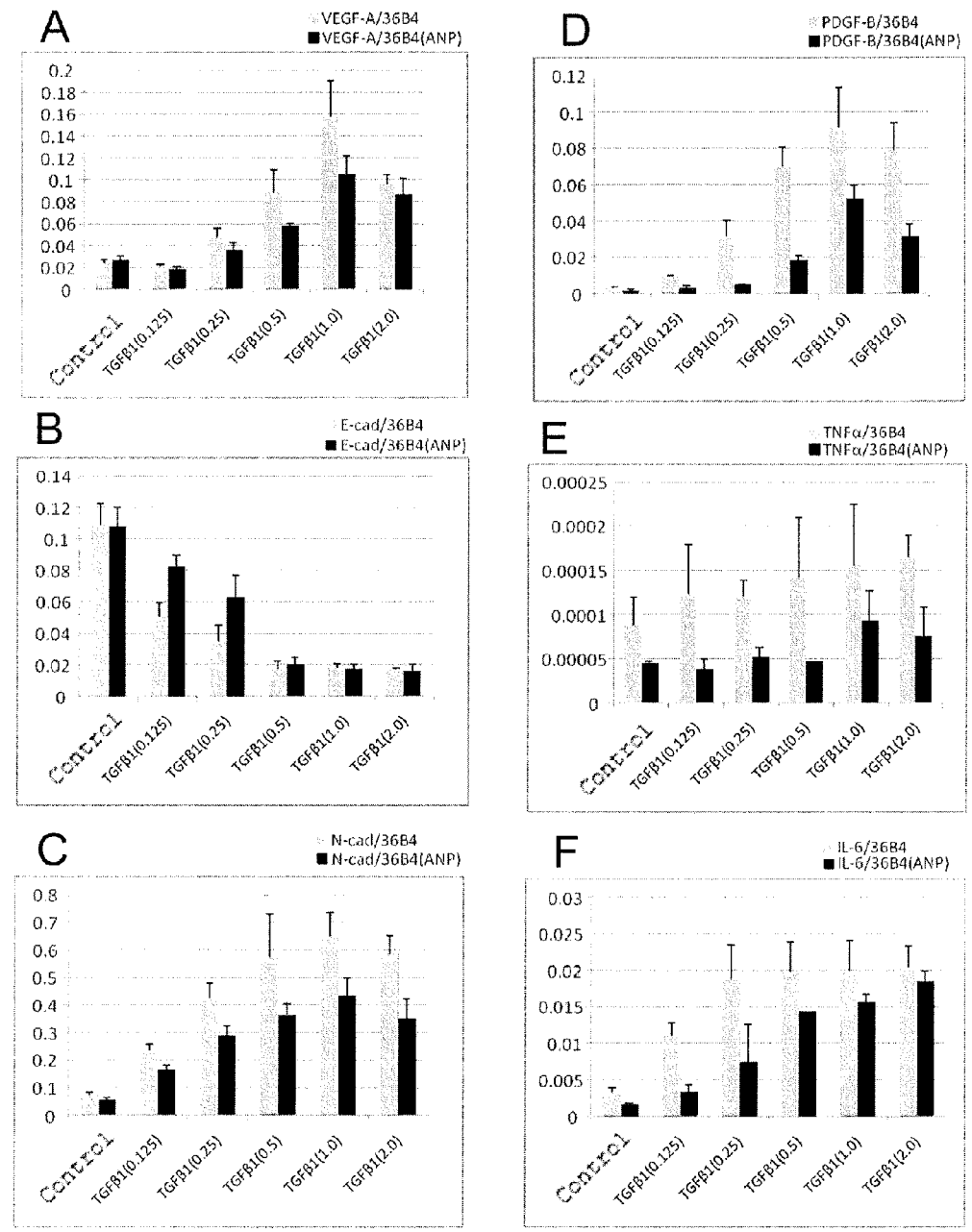
FIG. 3 shows graphs showing the gene expression of each factor (FIG. 3A: VEGF-A, FIG. 3B: E-cadherin (E-cad), FIG. 3C: N-cadherin (N-cad), FIG. 3D: PDGF-B, FIG. 3E: TNF-α, and FIG. 3F: IL-6) as an indicator of EMT based on the mRNA level responding to stimulation of A549 cells by 0.125, 0.25, 0.5, 1.0, and 2.0 ng/mL of TGF-β1 in the presence or absence of 1 μM hANP. In each graph, the horizontal axis indicates the TGF-β1 concentrations and the vertical axis indicates the mRNA level (the ratio of the mRNA amount of the intended gene to that of the 36B4 gene). In each graph, the gene expression in the absence of 1 μM hANP is shown by gray bars, and the gene expression in the presence of 1 μM hANP is shown by black bars.

Then, total RNA was recovered from the above prepared ANP group and control group using TRIZOL total RNA isolation reagent (made by Invitrogen), cDNA was synthesized using reverse transcriptase, and the mRNA levels of E-cadherin, N-cadherin, VEGF-A, PDGF-B, TNF-α, and IL-6 were measured by quantitative RT-PCR. The results of the mRNA level measurement are shown in FIG. 3. The mRNA level of each intended gene was calculated as the relative ratio of the mRNA amount of the gene to that of the housekeeping gene 36B4 measured at the same time. In the Examples below, unless otherwise stated, the mRNA levels were obtained through the same calculation.

Figure 4:
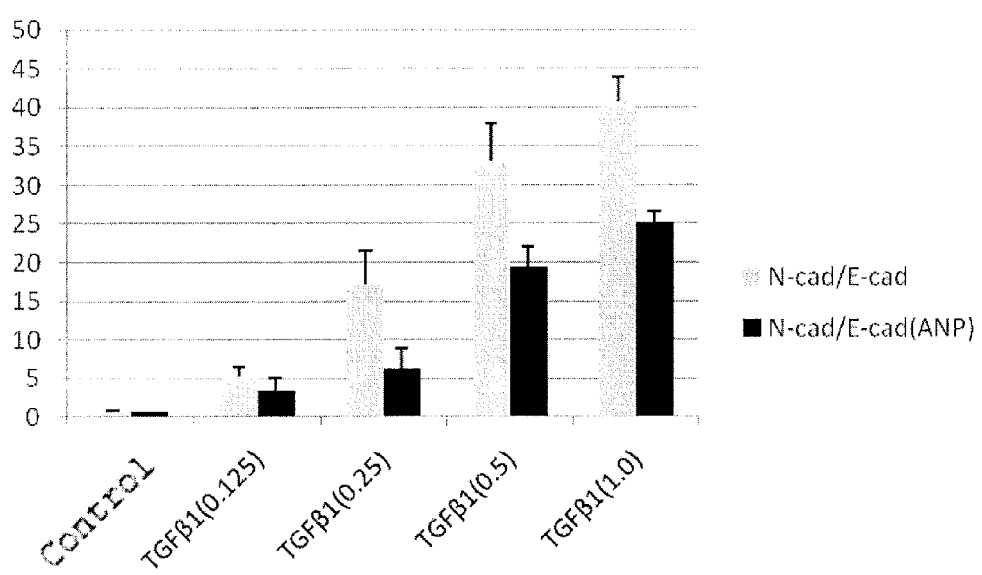
FIG. 4 shows a graph showing the expression ratio of N-cadherin to E-cadherin (N-cad/E-cad) responding to stimulation of A549 cells by 0.125, 0.25, 0.5, and 1.0 ng/mL of TGF-β1 in the presence or absence of 1 μM hANP. The horizontal axis indicates the TGF-β1 concentrations and the vertical axis indicates the expression ratio of N-cadherin to E-cadherin (N-cad/E-cad). The expression ratio (N-cad/E-cad) in the absence of 1 μM hANP is shown by gray bars, and the expression ratio (N-cad/E-cad) in the presence of 1 μM hANP is shown by black bars.

It is known that in EMT, the expression of E-cadherin decreases while the expression of N-cadherin increases. The expression ratio of the two kinds of cadherin (N-cad/E-cad) is considered to be useful as an indicator of the degree of EMT. The ratios are shown in FIG. 4.

Figure 2:
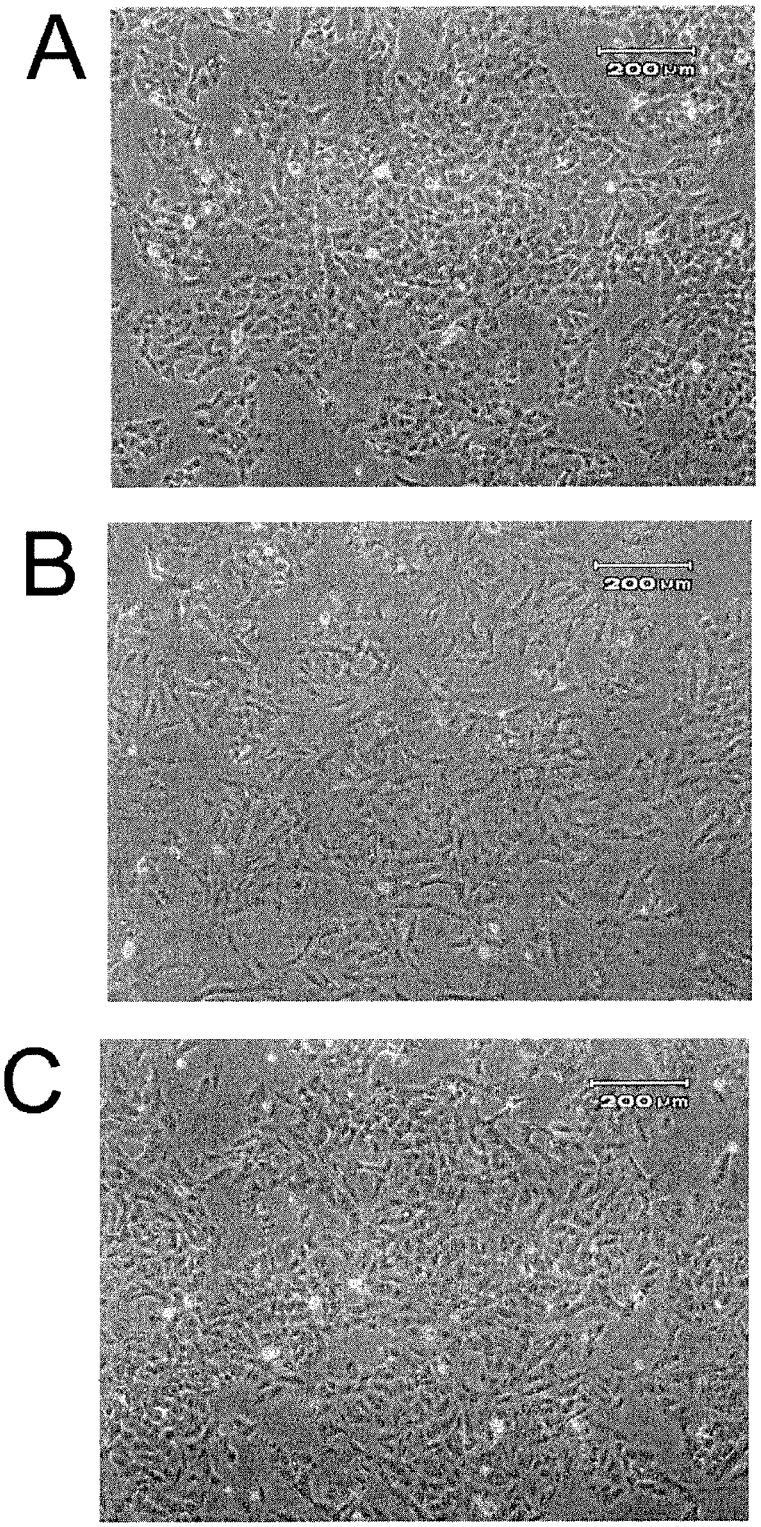
FIG. 2 shows micrographs showing the morphological change of A549 cells responding to stimulation by TGF-β1 in the presence (FIG. 2C) or absence (FIG. 2B) of 1 μM hANP (FIG. 2A: non-stimulated A549 cells (control), FIG. 2B: TGF-β1 (1 ng/mL), FIG. 2C: hANP (1 μM)+TGF-β1 (1 ng/mL)).

As shown in FIG. 2, 1 µM of hANP (FIG. 2C) significantly suppressed the morphological change in the cells (change to spindle shape similar to that of mesenchymal components as shown in FIG. 2B) associated with EMT induced by the TGF-β1 stimulus. Also, as shown in FIG. 3, hANP significantly suppressed the gene expression of the growth factors (VEGF-A, PDGF-B) and the inflammatory cytokines (TNF-α, IL-6) increased by EMT induced by the TGF-β1 stimulus. Also, hANP significantly suppressed increase in the expression of N-cadherin induced by the TGF-β1 stimulus and inhibited decrease in the expression of E-cadherin induced by the same stimulus. As a result, as shown in FIG. 4, the expression ratio of N-cad/E-cad, which is an important indicator of EMT, significantly decreased in the presence of 1 µM hANP. The same experiment using H460 cells derived from large cell lung carcinoma showed similar results.

Further, similar experiments were conducted using, instead of hANP as a test substance, hBNP (final concentration: 1 µM), CD-NP (final concentration: 10 µM (see Deborah et al., *J. Biol. Chem.*, vol. 289, No. 50, 35003-35009, 2008), and LKL-ANP (final concentration: 1 µM (a mutant in which the amino acids at positions 10 to 12 of hANP are replaced with LKL (see Furuya, M. et al., *Biochem. Biophys. Res. Commun.*, 183 (3), 964-969, 1992))) were used. As a result, in terms of the value of E-cad/Ncad, the ratios of suppression of EMT induced by TGF-β1 was 44.8% (BNP), 37.7% (CD-NP), and 52.9% (LKL-ANP). Thus, various kinds of the GC-A agonists showed an action of suppressing the EMT of tumor cells.

In the case where the same experiment was conducted using hCNP-22 instead of hANP, the form of the cells, and the expression level of each cytokine, growth factor, and cadherin were the same as those of the control.

Thus, hANP, hBNP, etc. as a GC-A agonist at a concentration of 1 μM showed the effect of significantly suppressing EMT, which is an important phenomenon triggering the metastasis and exacerbation of cancer. However, hCNP-22 as a CG-B-specific agonist did not show such an effect at all.

Example 3

The Effect of CNP on Production of Cancer Exacerbation Factors by CAF

Using a 6-well dish, the CAFs were cultured at 5×10$^4$ cells/well, and the culture medium was replaced with DMEM culture medium containing 1% FBS the next day. After 24 hours of culture, the cells were used in the following experiment.

Figure 5:
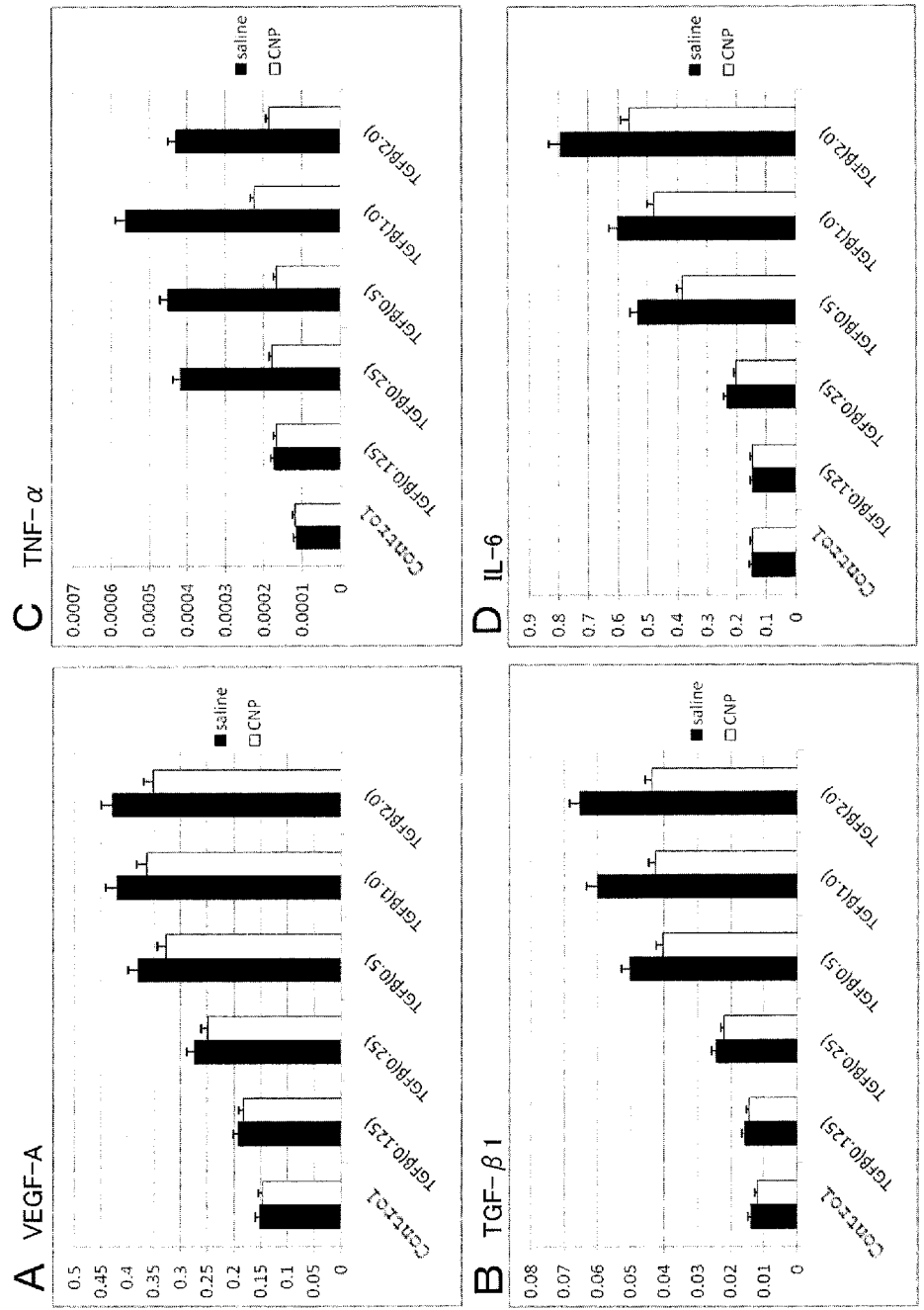
FIG. 5 shows graphs showing the gene expression of various cytokines and growth factors associated with the exacerbation of cancer (FIG. 5A: VEGF-A, FIG. 5B: TGF-β1, FIG. 5C: TNF-α, and FIG. 5D: IL-6) based on the mRNA level responding to stimulation of CAFs by 0.125, 0.25, 0.5, 1.0, and 2.0 ng/mL of TGF-β1 in the presence or absence of 1 μM hCNP-22. In each graph, the horizontal axis indicates the TGF-β1 concentrations and the vertical axis indicates the mRNA level (the ratio of the mRNA amount of the intended gene to that of the 36B4 gene). In each graph, the gene expression in the absence of 1 μM hCNP-22 is shown by black bars, and the gene expression in the presence of 1 μM hCNP-22 is shown by white bars.

A CNP group (a hCNP-22 solution was added (final concentration: 1 μM)) and a control group (the same amount of physiological saline was added) were prepared, and after 2 hours from the addition (of the hCNP-22 solution or the physiological saline) to the CAFs, TGF-β1 was added so that the final concentration would be 0.125, 0.25, 0.5, 1.0, and 2.0 ng/mL. After 24 hours had passed, total RNA was recovered using TRIZOL total RNA isolation reagent, cDNA was synthesized using reverse transcriptase, and the mRNA levels of VEGF-A, TGF-β1, TNF-α, and IL-6 were measured by quantitative RT-PCR. The results of the mRNA level measurement are shown in FIG. 5. As shown in FIG. 5, the added hCNP-22 significantly suppressed the gene expression of the growth factors (VEGF-A, TGF-β1) and the inflammatory cytokines (TNF-α, IL-6), of which expressions are increased by the TGF-β1 stimulus.

In the case where the same experiment was conducted using hANP or hBNP instead of hCNP-22, no differences were found between the presence and the absence of hANP or hBNP. That is, hANP and hBNP did not show any effect on CAFs.

Thus, hCNP-22 as a GC-B agonist at a concentration of 1 μM showed the effect of suppressing the positive control of representative cells in cancer stroma, namely CAFs, on cancer cells. However, hANP and hBNP as CG-A-specific agonists did not show such an effect.

The results of Examples 1 to 3 showed that stimulus specific to a GC-A receptor suppresses the exacerbation of cancer cells induced by EMT and that stimulus specific to a GC-B receptor suppresses the production of cancer exacerbation factors by CAFs.

Example 4

The Effects of ANP and CNP on Co-Culture System of Cancer Cells and CAFs

Based on the above results, the effects of a GC-A agonist and a GC-B agonist in a co-culture system where tumor cells and CAFs coexist in a single culture system as in an actual tumor tissue were examined.

In a 6-well dish, the A549 cells were cultured at 1×10$^5$ cells/well. The culture medium was replaced with DMEM culture medium free from FBS the next day, and the cells were further cultured for 24 hours. In a 6-well dish having a cell culture insert (1.0 μm pore size, made by BD), the CAFs were cultured at 5×10$^4$ cells/well. The culture medium was replaced with DMEM culture medium containing 1% FBS the next day, and the cells were further cultured for 24 hours. To each culture medium of the two kinds of cells, test substances were separately added to prepare test substance addition groups. Control groups with no test substance were also prepared. After two hours of culture, these were subjected to co-culture. The test substance addition groups were ANP groups containing hANP at a final concentration of 1 μM, CNP groups containing hCNP-22 at a final concentration of 1 μM, and ANP+CNP groups containing both hANP and hCNP-22 each at a final concentration of 1 μM. Each of the groups were prepared by adding the test substance to each culture medium of the two kinds of cells.

Figure 6:
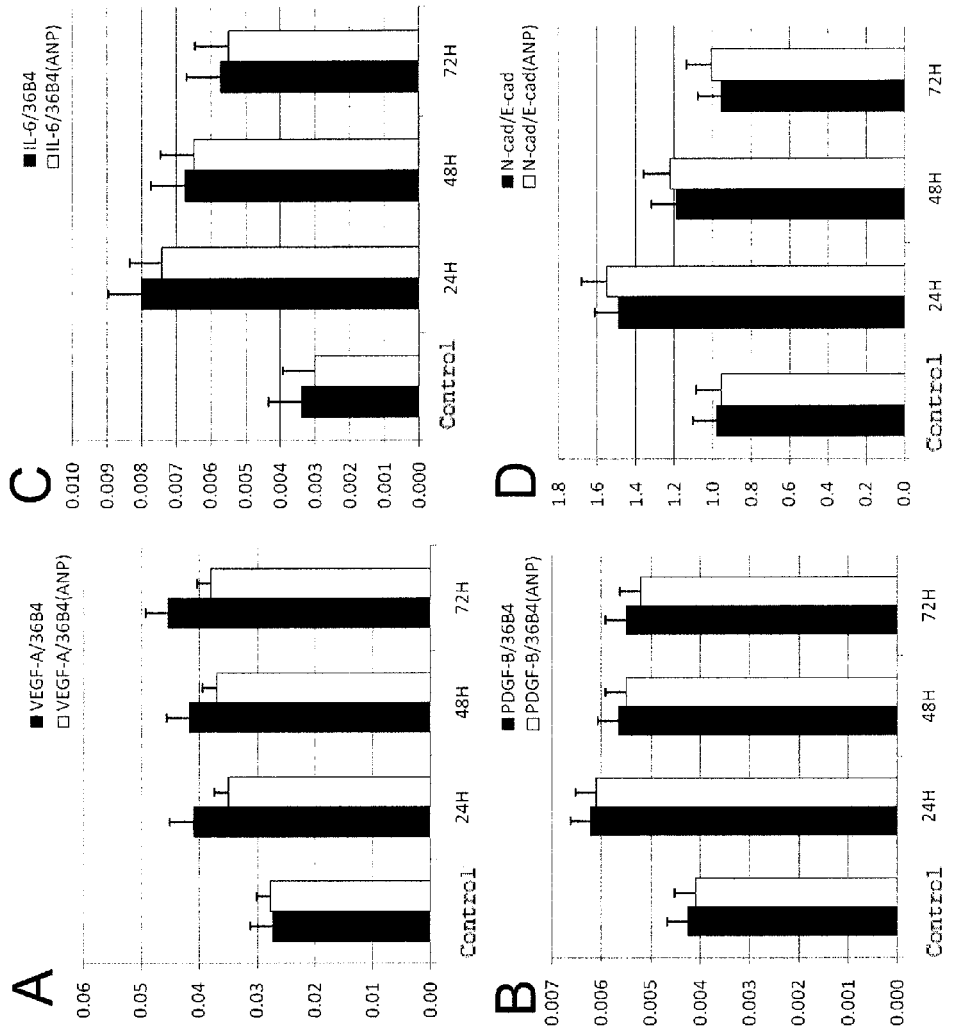
FIG. 6 shows graphs showing the gene expression levels of various growth factors and cytokine in A549 cells co-cultured with CAFs for 24, 48, and 72 hours (FIG. 6A: VEGF-A, FIG. 6B: PDGF-B, FIG. 6C: IL-6) in the presence or absence of 1 μM hANP as a test substance and showing the expression ratio of N-cadherin to E-cadherin:N-cad/E-cad (FIG. 6D). In each graph, the horizontal axis indicates the duration (hours) of co-culture and the vertical axis indicates the mRNA level (the ratio of the mRNA amount of the intended gene to that of the 36B4 gene) in FIGS. 6A to 6C and the ratio of N-cad/E-cad on the mRNA level in FIG. 6D. In each graph, the results in the absence of the test substance are shown by black bars, and the results in the presence of the test substance are shown by white bars.
Figure 7:
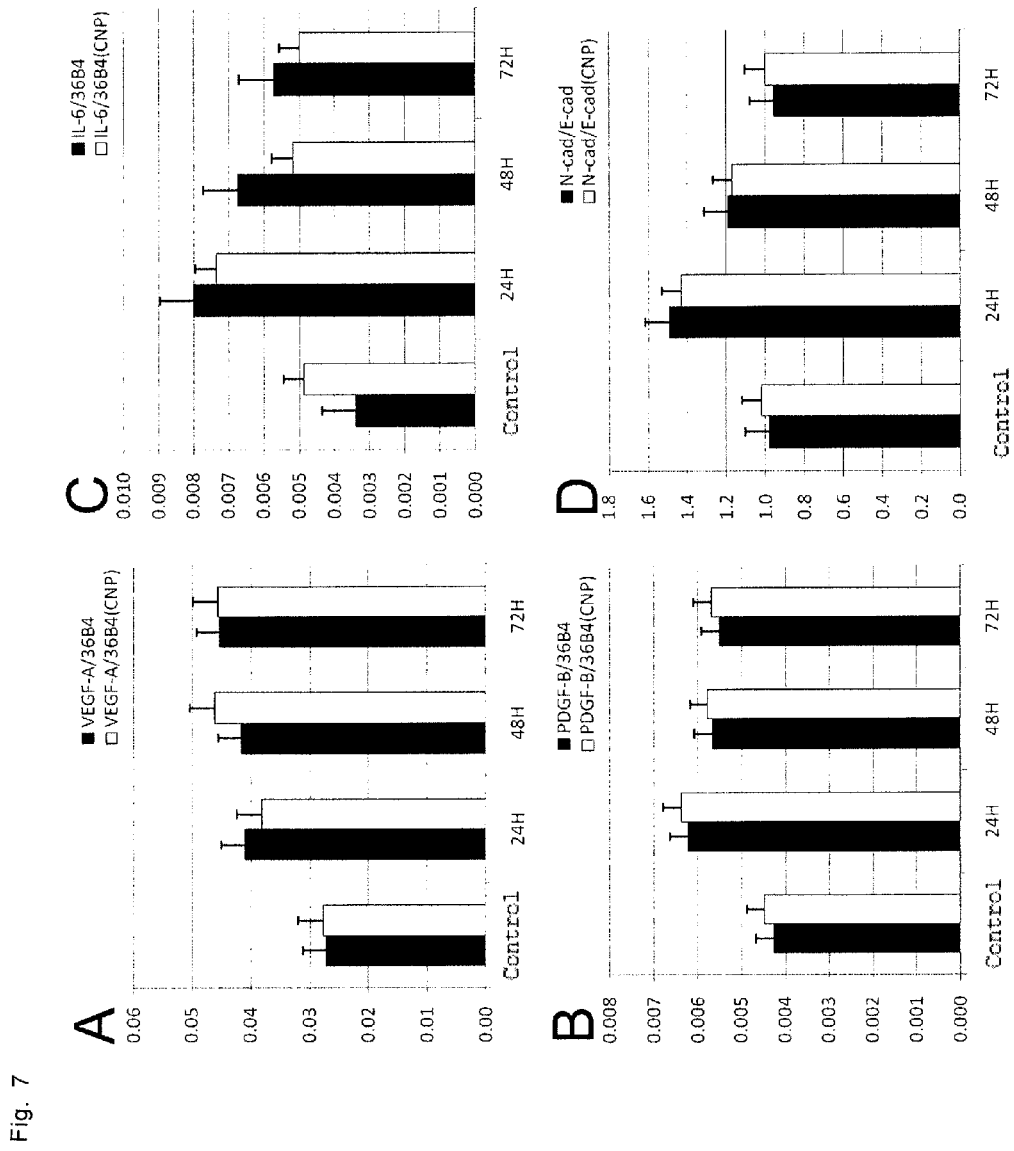
FIG. 7 shows graphs showing the gene expression levels of various growth factors and cytokine in A549 cells co-cultured with CAFs for 24, 48, and 72 hours (FIG. 7A: VEGF-A, FIG. 7B: PDGF-B, FIG. 7C: IL-6) in the presence or absence of 1 μM hCNP-22 as a test substance and showing the expression ratio of N-cadherin to E-cadherin:N-cad/E-cad (FIG. 7D). In each graph, the horizontal axis indicates the duration (hours) of co-culture and the vertical axis indicates the mRNA level (the ratio of the mRNA amount of the intended gene to that of the 36B4 gene) in FIGS. 7A to 7C and the ratio of N-cad/E-cad on the mRNA level in FIG. 7D. In each graph, the results in the absence of the test substance are shown by black bars, and the results in the presence of the test substance are shown by white bars.
Figure 8:
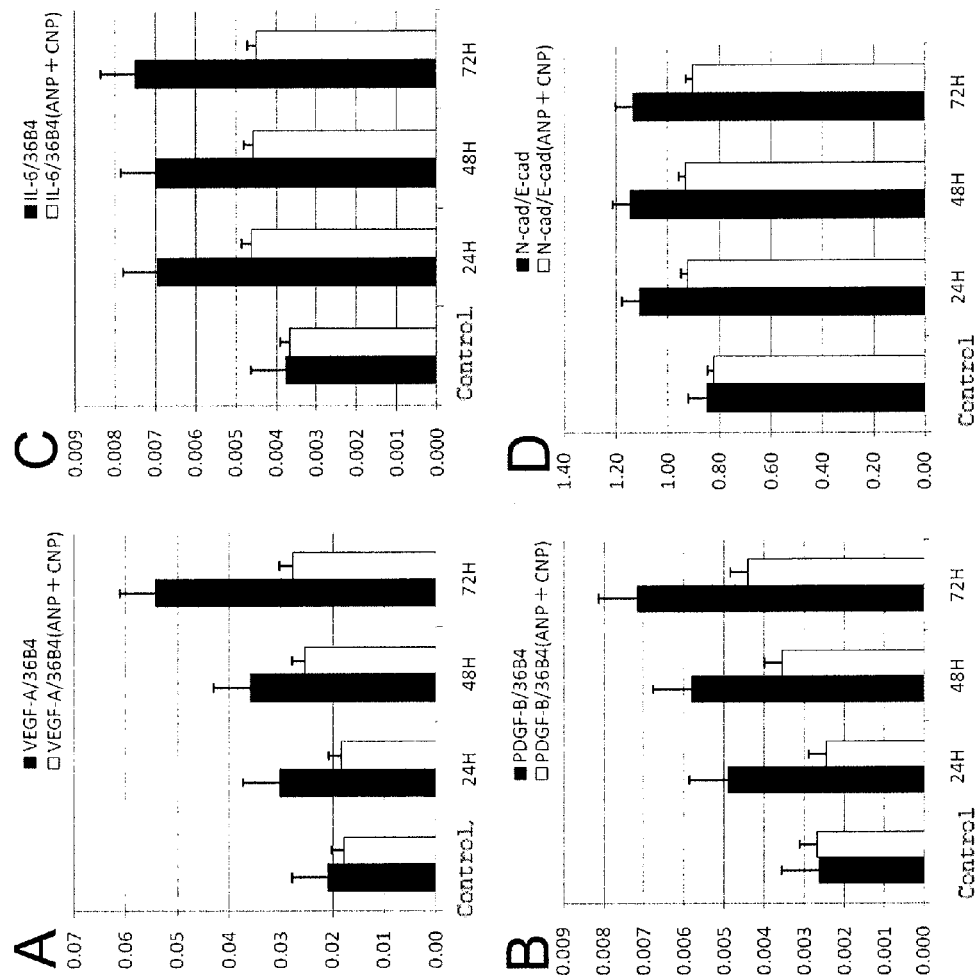
FIG. 8 shows graphs showing the gene expression levels of various growth factors and cytokine in A549 cells co-cultured with CAFs for 24, 48, and 72 hours (FIG. 8A: VEGF-A, FIG. 8B: PDGF-B, FIG. 8C: IL-6) in the presence or absence of both 1 μM hANP and 1 μM hCNP-22 as test substances and showing the expression ratio of N-cadherin to E-cadherin:N-cad/E-cad (FIG. 8D). In each graph, the horizontal axis indicates the duration (hours) of co-culture and the vertical axis indicates the mRNA level (the ratio of the mRNA amount of the intended gene to that of the 36B4 gene) in FIGS. 8A to 8C and the ratio of N-cad/E-cad on the mRNA level in FIG. 8D. In each graph, the results in the absence of the test substances are shown by black bars, and the results in the presence of the test substances are shown by white bars.

On the 6-well dish of A549 cells treated as above, the above cell culture insert with the CAFs was placed to prepare a co-culture experimental model where only the culture media could pass through the cell culture insert. After 24, 48, and 72 hours of culture, total RNA of the A549 cells only was recovered, cDNA was synthesized, and the mRNA levels of E-cadherin, N-cadherin, VEGF-A, PDGF-B, and IL-6 were measured by quantitative RT-PCR (FIGS. 6 to 8). The experiment using ANP alone (ANP groups: FIG. 6), the experiment using CNP alone (CNP groups: FIG. 7), and the experiment using ANP and CNP in combination (ANP+CNP group: FIG. 8) were independently conducted, where control groups were separately set for each experiment.

ANP alone and CNP alone could not suppress the gene expression of the growth factors (VEGF-A, PDGF-B) or inflammatory cytokine (IL-6), the expression of which increased in the co-culture (FIGS. 6 and 7). However, as shown in FIG. 8, simultaneous addition of ANP and CNP suppressed the expression of the growth factors and the cytokine at any time of 24, 48, and 72 hours. In addition, regarding the expression ratio of N-cadherin/E-cadherin (N-cad/E-cad), which is an indicator of EMT, simultaneous addition of ANP and CNP decreased the ratio, that is, suppressed the EMT although each of the test substances did not show any effect when administered alone.

That is, the effect of hANP, which exerts its effects on A549 cells only, is considered to have been decreased by the growth factors and the cytokine produced by the CAFs in the co-culture with the CAFs. Similarly, the effect of hCNP-22, which exerts its effects on CAFs only, is considered to have been decreased by the growth factors and the cytokine produced by the A549 cells in the co-culture with the A549 cells.

In contrast, the use of hANP and hCNP-22 in combination could exert effects on both A549 cells and CAFs, and thereby exerted the effects of suppressing the production of the growth factors and the cytokine and suppressing EMT in the co-culture.

Example 5

The Effects of ANP and CNP on Mouse Models Having Transplanted Cancer Cells and CAFs In this Example and Example 6, 5-week-old male immunodeficient mice (KSN mice, Japan SLC, Inc.) were used. The osmotic pumps used were MODEL2004 (for 28-day administration) made by ALZET (Cupertino, Calif.).

Immunodeficient mice into which the osmotic pump containing physiological saline was subcutaneously implanted in the back were assigned to the control group. Similarly, groups of mice having a subcutaneously implanted osmotic pump containing hANP and hCNP-22 for administration at 0.125

μg/kg/min (low dosage ANP+CNP group) or 0.5 μg/kg/min (high dosage ANP+CNP group) were prepared.

A mixed suspension of the A549 cells and the CAFs was prepared using DMEM free from FBS so as to contain the A549 cells at 1×10⁶ cells/100 μL and the CAFs at 0.5×10⁶ cells/100 μL. The mixed suspension in an amount of 100 μL per mouse was subcutaneously injected in the back of the above mice. The tumor size at the cell injection site was measured weekly, and tumor volume was calculated according to the following estimate equation (FIG. 9).

$$\text{Tumor volume}(mm^3) = (\pi/6) \times d^3$$

d=average of length and width (mm)

Figure 9:
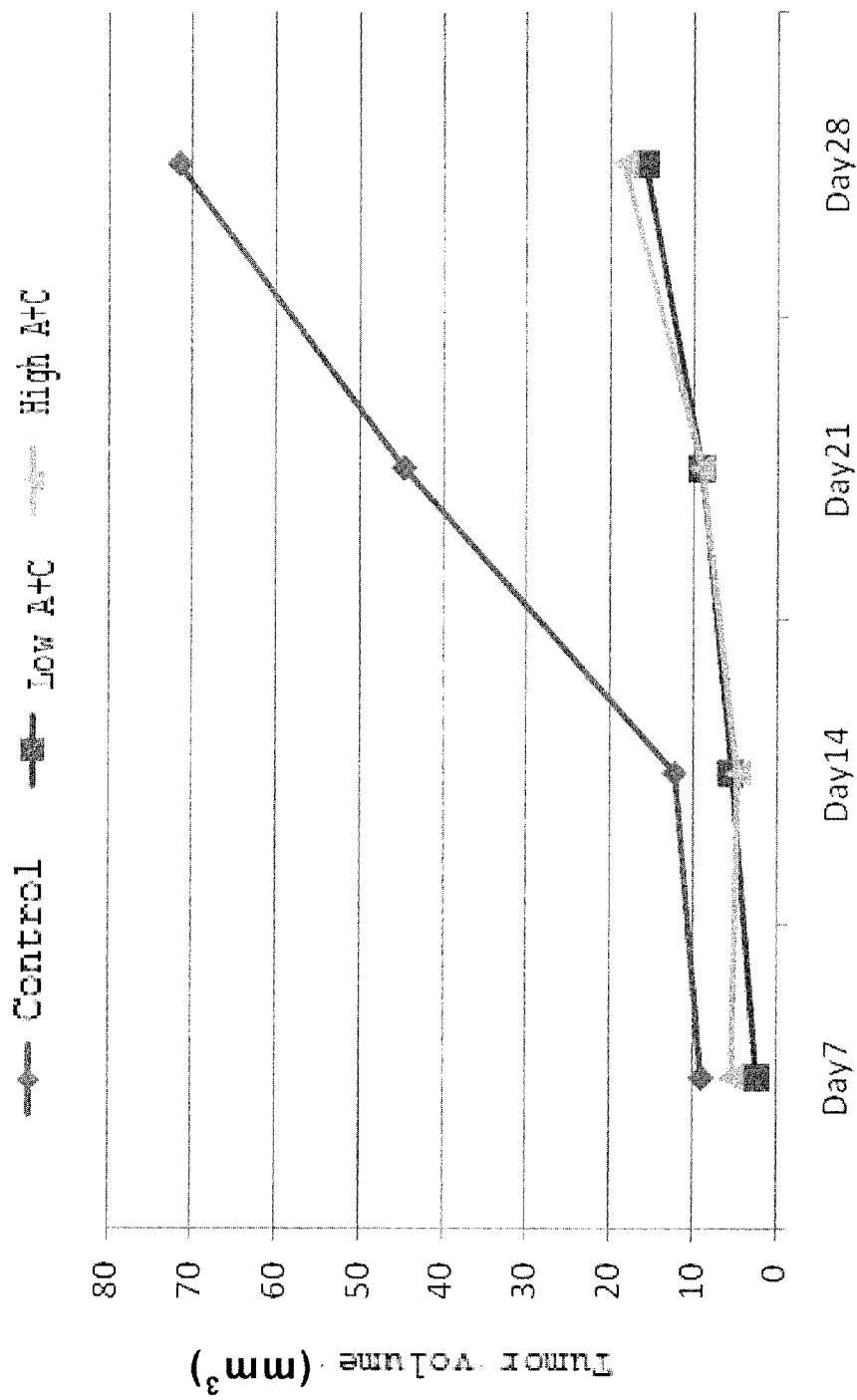
FIG. 9 is a graph showing change in the tumor volume of mice to which a mixed suspension of A549 cells and CAFs was transplanted (control group (diamonds), low dosage ANP+CNP administration group (both hANP and hCNP-22 were continuously administered at 0.125 µg/kg/min: squares), high dosage ANP+hCNP-22 administration group (both hANP and hCNP-22 were continuously administered at 0.5 µg/kg/min: triangles)) at 7, 14, 21, and 28 days after transplantation. In the graph, the horizontal axis indicates the number of days elapsed after the suspension transplantation and the vertical axis indicates the tumor volume (mm$^3$).

FIG. 9 shows that tumor growth was significantly suppressed by the administration of hANP and hCNP-22 in combination as compared to the control. In this case, the suppression effect was observed in the low dosage administration group to the same degree as in the high dosage administration group.

Example 6

The Effects of ANP and CNP on Mouse Models Having Transplanted Cancer Cells and CAFs (2)

The administration of hANP and hCNP to the same tumor transplantation models as in Example 5 was started after tumor tissue was established, and the effects were examined.

A mixed suspension of the A549 cells and the CAFs was prepared using DMEM free from FBS so as to contain the A549 cells at 1×10⁶ cells/100 μL and the CAFs at 0.5×10⁶ cells/100 μL. The mixed suspension in an amount of 100 μL per mouse was subcutaneously injected in the back of the immunodeficient mice. In the experiment, a control group, as reference for comparison with the administration groups, to which a suspension of only the A549 cells (1.5×10⁶ cells/mouse) was injected (A549 group) was examined.

After 2 weeks of observation from the injection of the cell suspension, the mice to which the mixed suspension had been injected were randomly divided into 4 groups (control group, ANP group, CNP group, and ANP+CNP group), and an osmotic pump appropriately adjusted for each group as shown below was subcutaneously implanted to start administration.

Control group and A549 group: physiological saline was administered
ANP group: hANP was administered at 0.5 μg/kg/min
CNP group: hCNP-22 was administered at 2.5 μg/kg/min
ANP+CNP group: hANP was administered at 0.5 μg/kg/min and hCNP-22 was administered at 2.5 μg/kg/min Observation was further continued for 4 weeks after the start of administration, the tumor size at the cell injection site was measured weekly, and tumor volume was calculated in the same way as in Example 5 (FIG. 10).

FIG. 10 shows that, the tumor volume of the control group, to which the mixture of the A549 cells and the CAFs were transplanted, significantly increased as compared to that of the A549 group, to which only tumor cells had been transplanted, showing that the interaction between tumor cells and CAFs accelerates the growth of tumors.

Even when administered alone, hANP and hCNP-22, as compared with the control group, showed an effect of tumor growth suppression. Further, when administered in combination (ANP+CNP group), hANP and hCNP-22 most significantly suppressed tumor growth. In this case, the degree of tumor volume increase was even lower than that in the case where only the A549 cells had been transplanted. Thus, it was shown that suppressing tumor cells and CAFs at the same time to break the vicious circle formed by these cells is quite effective in suppressing the growth and exacerbation of a malignant tumor, that is, treating a malignant tumor.

The results of the above Examples showed the effect of the combined use of a GC-A agonist and a GC-B agonist as schematically shown in FIG. 12. That is, humoral factors, such as VEGF, PDGF-B, and IL-6, stimulate CAFs, and thereby increase the production of VEGF, bFGF, TNF-α, IL-6, etc. from the CAFs. The humoral factors produced from the CAFs further stimulate cancer cells. The exacerbation of a tumor in tumor tissue is considered to proceed in such a vicious circle. A GC-A agonist, such as ANP, exerts an action on cancer cells and has an effect of suppressing the production of the humoral factors. Meanwhile, a GC-B agonist, such as CNP, exerts an action on CAFs and has an effect of suppressing the production of the humoral factors. Therefore, in the present invention, an effective treatment of a malignant tumor is achieved by a combination of a GC-A agonist and a GC-B agonist, the combination acting on tumor tissue and breaking the vicious circle formed by cancer cells and CAFs. That is, allowing a GC-A agonist, which suppresses EMT of cancer cells, and a GC-B agonist, which suppresses transformation of CAFs, to act at the same time on tumor tissue, where cancer cells and CAFs coexist as a mixture, breaks the vicious circle which is formed by cancer cells and CAFs and enables an effective treatment or prevention of cancer.

Herein, as representative tumor cells in the Examples, human lung cancer A549 cells and H460 cells were adopted. However, not only in the lung cancer cells, but also in various kinds of tumor cells including PANC1 of pancreatic cancer (epithelioid carcinoma), PC3 of prostatic cancer (adenocarcinoma), GCIY of gastric cancer (adenocarcinoma), CaCo2 of colon cancer (colorectal adenocarcinoma), and OVCAR-3 of ovarian cancer (adenocarcinoma), the expression of a GC-A receptor was confirmed. Therefore, the treatment using the combination of a GC-A agonist and a GC-B agonist exerts effects on various kinds of tumors.

The invention claimed is:

1. A method for treating a malignant tumor or for suppressing or preventing the exacerbation thereof, comprising administering an effective amount of an atrial natriuretic peptide consisting of the amino acid sequence of SEQ ID NO: 1 and an effective amount of a c-type natriuretic peptide consisting of the amino acid sequence of SEQ ID NO: 7 in combination, wherein the effective amount of atrial natriuretic peptide is 0.01 µg kg$^{-1}$ min$^{-1}$ or more and 0.2 µg kg$^{-1}$ min$^{-1}$ or less and the effective amount of c-type natriuretic peptide is 0.01 µg kg$^{-1}$ min$^{-1}$ or more and 1.0 µg kg$^{-1}$ min$^{-1}$ or less, and wherein the effective amount is administered continuously for at least three days.

2. The method according to claim 1, wherein the atrial natriuretic peptide and the c-type natriuretic peptide are administered simultaneously.

3. The method according to claim 1, wherein the atrial natriuretic peptide and the c-type natriuretic peptide are administered in a single formulation.

4. A method for treating a malignant tumor or for suppressing or preventing the exacerbation thereof, which comprises administering an agent which comprises atrial natriuretic peptide consisting of the amino acid sequence of SEQ ID NO: 1 as an active ingredient at an amount which is 0.01 µg kg$^{-1}$ min$^{-1}$ or more and 0.2 µg kg$^{-1}$ min$^{-1}$ or less and the agent is administered in combination with a c-type natriuretic peptide consisting of the amino acid sequence of SEQ ID NO: 7 at an amount which is 0.01 µg kg$^{-1}$ min$^{-1}$ or more and 1.0 µg kg$^{-1}$ min$^{-1}$ or less and wherein the agent and c-natriuretic peptide are administered continuously for at least three days.

5. A method for treating a malignant tumor or for suppressing or preventing the exacerbation thereof, the method comprising administering a medicinal agent which comprises a c-type natriuretic peptide consisting of the amino acid sequence of SEQ ID NO: 7 as an active ingredient at an amount which is 0.01 µg kg$^{-1}$ min$^{-1}$ or more and 1.0 µg kg$^{-1}$ min$^{-1}$ or less and said medicinal agent is to be administered in combination with an atrial natriuretic peptide consisting of the amino acid sequence of SEQ ID NO: 1 at an amount which is 0.01 µg kg$^{-1}$ min$^{-1}$ or more and 0.2 µg kg$^{-1}$ min$^{-1}$ or less and wherein the medicinal agent and atrial natriuretic peptide are administered continuously for at least three days.

* * * * *

SEQUENCE LISTING

<160> NUMBER OF SEQ ID NOS: 35

<210> SEQ ID NO 1
<211> LENGTH: 28
<212> TYPE: PRT
<213> ORGANISM: Homo sapiens

<400> SEQUENCE: 1

Ser Leu Arg Arg Ser Ser Cys Phe Gly Gly Arg Met Asp Arg Ile Gly
1               5                   10                  15

```
Ala Gln Ser Gly Leu Gly Cys Asn Ser Phe Arg Tyr
            20                  25

<210> SEQ ID NO 2
<211> LENGTH: 28
<212> TYPE: PRT
<213> ORGANISM: Rattus rattus

<400> SEQUENCE: 2

Ser Leu Arg Arg Ser Ser Cys Phe Gly Gly Arg Ile Asp Arg Ile Gly
1               5                   10                  15

Ala Gln Ser Gly Leu Gly Cys Asn Ser Phe Arg Tyr
            20                  25

<210> SEQ ID NO 3
<211> LENGTH: 32
<212> TYPE: PRT
<213> ORGANISM: Homo sapiens

<400> SEQUENCE: 3

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 4
<211> LENGTH: 32
<212> TYPE: PRT
<213> ORGANISM: Sus scrofa

<400> SEQUENCE: 4

Ser Pro Lys Thr Met Arg Asp Ser Gly Cys Phe Gly Arg Arg Leu Asp
1               5                   10                  15

Arg Ile Gly Ser Leu Ser Gly Leu Gly Cys Asn Val Leu Arg Arg Tyr
            20                  25                  30

<210> SEQ ID NO 5
<211> LENGTH: 45
<212> TYPE: PRT
<213> ORGANISM: Rattus rattus

<400> SEQUENCE: 5

Ser Gln Asp Ser Ala Phe Arg Ile Gln Glu Arg Leu Arg Asn Ser Lys
1               5                   10                  15

Met Ala His Ser Ser Cys Phe Gly Gln Lys Ile Asp Arg Ile Gly
            20                  25                  30

Ala Val Ser Arg Leu Gly Cys Asp Gly Leu Arg Leu Phe
        35                  40                  45

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      ring structure peptide of ANPs and BNPs
<220> FEATURE:
<221> NAME/KEY: MOD_RES
<222> LOCATION: (4)..(5)
<223> OTHER INFORMATION: Any naturally occurring amino acid or
      artificial amino acid mimetic
<220> FEATURE:
<221> NAME/KEY: MOD_RES
<222> LOCATION: (6)..(6)
```

```
<223> OTHER INFORMATION: Met, Leu or Ile
<220> FEATURE:
<221> NAME/KEY: MOD_RES
<222> LOCATION: (10)..(14)
<223> OTHER INFORMATION: Any naturally occurring amino acid or
      artificial amino acid mimetic
<220> FEATURE:
<221> NAME/KEY: MOD_RES
<222> LOCATION: (18)..(20)
<223> OTHER INFORMATION: Any naturally occurring amino acid or
      artificial amino acid mimetic

<400> SEQUENCE: 6

Cys Phe Gly Xaa Xaa Xaa Asp Arg Ile Xaa Xaa Xaa Xaa Xaa Leu Gly
1               5                   10                  15

Cys Xaa Xaa Xaa Arg
            20

<210> SEQ ID NO 7
<211> LENGTH: 22
<212> TYPE: PRT
<213> ORGANISM: Homo sapiens

<400> SEQUENCE: 7

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 8
<211> LENGTH: 53
<212> TYPE: PRT
<213> ORGANISM: Homo sapiens

<400> SEQUENCE: 8

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 9
<211> LENGTH: 22
<212> TYPE: PRT
<213> ORGANISM: Gallus gallus

<400> SEQUENCE: 9

Gly Leu Ser Arg Ser Cys Phe Gly Val Lys Leu Asp Arg Ile Gly Ser
1               5                   10                  15

Met Ser Gly Leu Gly Cys
            20

<210> SEQ ID NO 10
<211> LENGTH: 22
<212> TYPE: PRT
<213> ORGANISM: Rana sp.

<400> SEQUENCE: 10

Gly Tyr Ser Arg Gly Cys Phe Gly Val Lys Leu Asp Arg Ile Gly Ala
1               5                   10                  15
```

```
Phe Ser Gly Leu Gly Cys
            20

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      ring structure peptide of CNP
<220> FEATURE:
<221> NAME/KEY: MOD_RES
<222> LOCATION: (4)..(4)
<223> OTHER INFORMATION: Leu or Val
<220> FEATURE:
<221> NAME/KEY: MOD_RES
<222> LOCATION: (11)..(11)
<223> OTHER INFORMATION: Ser or Ala
<220> FEATURE:
<221> NAME/KEY: MOD_RES
<222> LOCATION: (12)..(12)
<223> OTHER INFORMATION: Met, Phe or Glu

<400> SEQUENCE: 11

Cys Phe Gly Xaa Lys Leu Asp Arg Ile Gly Xaa Xaa Ser Gly Leu Gly
1               5                   10                  15

Cys

<210> SEQ ID NO 12
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric ANP (A) (SEQ ID NO;106) of
      US2010-305031 and WO2009/142307

<400> SEQUENCE: 12

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Val Gln Gln Arg
            20                  25                  30

Lys Glu Ser Lys Lys Pro Pro Ala Lys Leu Gln Pro Arg
        35                  40                  45

<210> SEQ ID NO 13
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric ANP (B) (SEQ ID NO;107) of
      US2010-305031 and WO2009/142307

<400> SEQUENCE: 13

Val Gln Gln Arg Lys Glu Ser Lys Lys Pro Pro Ala Lys Leu Gln Pro
1               5                   10                  15

Arg Ser Leu Arg Arg Ser Ser Cys Phe Gly Gly Arg Met Asp Arg Ile
            20                  25                  30

Gly Ala Gln Ser Gly Leu Gly Cys Asn Ser Phe Arg Tyr
        35                  40                  45

<210> SEQ ID NO 14
```

```
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric ANP (C) (SEQ ID NO;108) of
      US2010-305031 and WO2009/142307

<400> SEQUENCE: 14

Arg Pro Gln Leu Lys Ala Pro Pro Lys Lys Ser Glu Lys Arg Gln Gln
1               5                   10                  15

Val Ser Leu Arg Arg Ser Ser Cys Phe Gly Gly Arg Met Asp Arg Ile
            20                  25                  30

Gly Ala Gln Ser Gly Leu Gly Cys Asn Ser Phe Arg Tyr
        35                  40                  45

<210> SEQ ID NO 15
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric CNP (A) (SEQ ID NO;109) of
      US2010-305031 and WO2009/142307

<400> SEQUENCE: 15

Arg Pro Gln Leu Lys Ala Pro Pro Lys Lys Ser Glu Lys Arg Gln Gln
1               5                   10                  15

Val Cys Phe Gly Leu Lys Leu Asp Arg Ile Gly Ser Met Ser Gly Leu
            20                  25                  30

Gly Cys

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric CNP (B) (SEQ ID NO;110) of
      US2010-305031 and WO2009/142307

<400> SEQUENCE: 16

Cys Phe Gly Leu Lys Leu Asp Arg Ile Gly Ser Met Ser Gly Leu Gly
1               5                   10                  15

Cys Val Gln Gln Arg Lys Glu Ser Lys Lys Pro Pro Ala Lys Leu Gln
            20                  25                  30

Pro Arg

<210> SEQ ID NO 17
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric CNP (C) (SEQ ID NO;124) of
      US2010-305031 and WO2009/142307

<400> SEQUENCE: 17
```

```
Cys Phe Gly Leu Lys Leu Asp Arg Ile Gly Ser Met Ser Gly Leu Gly
1               5                   10                  15

Cys Val Gln Gln Arg Lys Glu Ser Lys Lys Pro Pro Ala Lys Leu Gln
                20                  25                  30

Pro Arg

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric CNP (D) (SEQ ID NO;125) of
      US2010-305031 and WO2009/142307

<400> SEQUENCE: 18

Gly Leu Ser Lys Gly Cys Phe Gly Leu Lys Leu Asp Arg Ile Gly Ser
1               5                   10                  15

Met Ser Gly Leu Gly Cys Val Gln Gln Arg Lys Glu Ser Lys Lys Pro
                20                  25                  30

Pro Ala Lys Leu Gln Pro Arg
        35

<210> SEQ ID NO 19
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric CNP (E) (SEQ ID NO;126) of
      US2010-305031 and WO2009/142307

<400> SEQUENCE: 19

Val Gln Gln Arg Lys Glu Ser Lys Lys Pro Pro Ala Lys Leu Gln Pro
1               5                   10                  15

Arg Cys Phe Gly Leu Lys Leu Asp Arg Ile Gly Ser Met Ser Gly Leu
                20                  25                  30

Gly Cys Val Gln Gln Arg Lys Glu Ser Lys Lys Pro Pro Ala Lys Leu
        35                  40                  45

Gln Pro Arg
    50

<210> SEQ ID NO 20
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric CNP (F) (SEQ ID NO;127) of
      US2010-305031 and WO2009/142307

<400> SEQUENCE: 20

Arg Pro Gln Leu Lys Ala Pro Pro Lys Lys Ser Glu Lys Arg Gln Gln
1               5                   10                  15

Val Cys Phe Gly Leu Lys Leu Asp Arg Ile Gly Ser Met Ser Gly Leu
                20                  25                  30

Gly Cys Val Gln Gln Arg Lys Glu Ser Lys Lys Pro Pro Ala Lys Leu
        35                  40                  45
```

Gln Pro Arg
    50

<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric CNP (G) (SEQ ID NO;128) of
      US2010-305031 and WO2009/142307

<400> SEQUENCE: 21

Val Gln Gln Arg Lys Glu Ser Lys Lys Pro Pro Ala Lys Leu Gln Pro
1               5                   10                  15

Arg Cys Phe Gly Leu Lys Leu Asp Arg Ile Gly Ser Met Ser Gly Leu
            20                  25                  30

Gly Cys

<210> SEQ ID NO 22
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric CNP (H) (SEQ ID NO;129) of
      US2010-305031 and WO2009/142307

<400> SEQUENCE: 22

Arg Pro Gln Leu Lys Ala Pro Pro Lys Lys Ser Glu Lys Arg Gln Gln
1               5                   10                  15

Val Cys Phe Gly Leu Lys Leu Asp Arg Ile Gly Ser Met Ser Gly Leu
            20                  25                  30

Gly Cys

<210> SEQ ID NO 23
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric CNP (I) (SEQ ID NO;130) of
      US2010-305031 and WO2009/142307
<220> FEATURE:
<223> OTHER INFORMATION: C-term amidated

<400> SEQUENCE: 23

Cys Phe Gly Leu Lys Leu Asp Arg Ile Gly Ser Met Ser Gly Leu Gly
1               5                   10                  15

Cys Val Gln Gln Arg Lys Glu Ser Lys Lys Pro Pro Ala Lys Leu Gln
            20                  25                  30

Pro Arg

<210> SEQ ID NO 24
<211> LENGTH: 39
<212> TYPE: PRT
<213> ORGANISM: Artificial Sequence
<220> FEATURE:
<223> OTHER INFORMATION: Description of Artificial Sequence: Synthetic

```
                            polypeptide
<220> FEATURE:
<223> OTHER INFORMATION: Chimeric CNP (J) (SEQ ID NO;157) of
      US2010-305031 and WO2009/142307

<400> SEQUENCE: 24

Gly Leu Ser Lys Gly Cys Phe Gly Leu Lys Leu Asp Arg Ile Gly Ser
1               5                   10                  15

Met Ser Gly Leu Gly Cys Val Gln Gln Arg Lys Asp Ser Lys Lys Pro
            20                  25                  30

Pro Ala Lys Leu Gln Pro Arg
        35

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric CNP (K) (SEQ ID NO;158) of
      US2010-305031 and WO2009/142307

<400> SEQUENCE: 25

Cys Phe Gly Leu Lys Leu Asp Arg Ile Gly Ser Met Ser Gly Leu Gly
1               5                   10                  15

Cys Ala Gly Ser Val Asp His Lys Gly Lys Gln Arg Lys Val Val Asp
            20                  25                  30

His Pro Lys Arg
        35

<210> SEQ ID NO 26
<211> LENGTH: 6
<212> TYPE: PRT
<213> ORGANISM: Homo sapiens

<400> SEQUENCE: 26

Ser Leu Arg Arg Ser Ser
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Lys Glu Ser Lys Lys
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Lys Asp Ser Lys Lys
1               5
```

```
<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Lys Ser Glu Lys Lys
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Lys Ser Asp Lys Lys
1               5

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Gln Gln Arg Lys Glu Ser Lys Lys Pro Pro Ala Lys Leu Gln Pro
1               5                   10                  15

Arg

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Pro Gln Leu Lys Ala Pro Pro Lys Lys Ser Glu Lys Arg Gln Gln
1               5                   10                  15

Val

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Val Gln Gln Arg Lys Asp Ser Lys Lys Pro Pro Ala Lys Leu Gln Pro
1               5                   10                  15

Arg

<210> SEQ ID NO 34
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 34

Ala Gly Ser Val Asp His Lys Gly Lys Gln Arg Lys Val Val Asp His
1               5                   10                  15

Pro Lys Arg

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Lys Ser Glu Lys Arg
1               5
```